US012667651B2

(12) United States Patent
Yuds et al.

(10) Patent No.: US 12,667,651 B2
(45) Date of Patent: Jun. 30, 2026

(54) DIALYSIS FLUID TESTING SYSTEM

(71) Applicant: Fresenius Medical Care Holdings, Inc., Waltham, MA (US)

(72) Inventors: David Yuds, Hudson, NH (US); Jun Yi, Norman, OK (US); Natalie Rebacz, Bartlesville, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 700 days.

(21) Appl. No.: 17/991,636

(22) Filed: Nov. 21, 2022

(65) Prior Publication Data

US 2023/0158216 A1 May 25, 2023

Related U.S. Application Data

(60) Provisional application No. 63/282,069, filed on Nov. 22, 2021.

(51) Int. Cl.
    *A61M 1/14* (2006.01)
    *A61M 1/16* (2006.01)
    (Continued)

(52) U.S. Cl.
    CPC .............. *A61M 1/154* (2022.05); *A61M 1/14* (2013.01); *A61M 1/1562* (2022.05);
    (Continued)

(58) Field of Classification Search
    CPC ...... A61M 1/14; A61M 1/154; A61M 1/1562; A61M 1/159; A61M 1/16; A61M 1/1609;

A61M 1/1619; A61M 1/28; A61M 1/287; A61M 1/3406; A61M 2205/12; A61M 2205/123; A61M 2205/18; A61M 2205/3306; A61M 2205/3313; A61M 2205/70; A61M 2205/702
See application file for complete search history.

(56) References Cited

U.S. PATENT DOCUMENTS

2003/0216677 A1 * 11/2003 Pan ........................ A61M 1/154
                                                      210/252
2019/0381231 A1    12/2019 Tsoory et al.
                            (Continued)

FOREIGN PATENT DOCUMENTS

EP          3281658          2/2018
EP          3643340          4/2020

OTHER PUBLICATIONS

International Preliminary Report on Patentability in International Appln. No. PCT/US2022/049149, mailed Jun. 6, 2024, 13 pages.
(Continued)

*Primary Examiner* — John Kim
(74) *Attorney, Agent, or Firm* — Fish & Richardson P.C.

(57) ABSTRACT

A method includes flowing spent dialysate through a spent dialysate line of a dialysis system into a fluid receptacle fluidly coupled to the spent dialysate line, reacting the spent dialysate with a chemical reagent contained within the fluid receptacle to generate a reacted sample, emitting electromagnetic radiation through the reacted sample using an emitter; detecting a level of one or more waste products present in the spent dialysate using a spectroscopy sensor positioned proximate the fluid receptacle.

28 Claims, 13 Drawing Sheets

(51) Int. Cl.
  *A61M 1/28* (2006.01)
  *A61M 1/34* (2006.01)

(52) U.S. Cl.
  CPC .......... *A61M 1/159* (2022.05); *A61M 1/1619* (2014.02); *A61M 1/28* (2013.01); *A61M 1/287* (2013.01); *A61M 1/16* (2013.01); *A61M 1/1609* (2014.02); *A61M 1/3406* (2014.02); *A61M 2205/12* (2013.01); *A61M 2205/123* (2013.01); *A61M 2205/18* (2013.01); *A61M 2205/3306* (2013.01); *A61M 2205/3313* (2013.01); *A61M 2205/70* (2013.01); *A61M 2205/702* (2013.01)

(56) References Cited

U.S. PATENT DOCUMENTS

| | | |
|---|---|---|
| 2021/0220541 A1 | 7/2021 | Gerber et al. |
| 2023/0248890 A1* | 8/2023 | Wang ...................... A61M 1/28 604/29 |

OTHER PUBLICATIONS

[No Author Listed], "Cancer Imaging: Chemical reaction reveals tumours," Nature, Aug. 2013, 500:380.
International Search Report and Written Opinion in International Appln. No. PCT/US2022/049149, mailed Mar. 13, 2023, 20 pages.
Wikipedia.org [online], "Raman spectroscopy," Aug. 2020, retrieved on Mar. 7, 2023, retrieved from URL <https://en.wikipedia.org/wiki/Raman_spectroscopy>, 21 pages.

* cited by examiner

DIALYSIS FLUID TESTING SYSTEM

CLAIM OF PRIORITY

This application claims priority under 35 USC § 119(e) to U.S. Patent Application Ser. No. 63/282,069, filed on Nov. 22, 2021, the entire contents of which are hereby incorporated by reference.

TECHNICAL FIELD

This disclosure relates to systems and methods for testing dialysis fluids.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a method includes flowing spent dialysate through a spent dialysate line of a dialysis system into a fluid receptacle fluidly coupled to the spent dialysate line, reacting the spent dialysate with a chemical reagent contained within the fluid receptacle to generate a reacted sample, emitting electromagnetic radiation through the reacted sample using an emitter; and detecting a level of one or more waste products present in the spent dialysate using a spectroscopy sensor positioned proximate the fluid receptacle.

Implementations can include one or more of the following features in any combination.

In some implementations, flowing the spent dialysate from the spent dialysate line into the fluid receptacle includes breaking a frangible connector to fluidly connect the spent dialysate line to the fluid receptacle.

In certain implementations, the frangible connector is broken by a frangible breaking mechanism of a dialysis machine of the dialysis system.

In some implementations, flowing the spent dialysate from the spent dialysate line into the fluid receptacle includes closing a first valve positioned along the spent dialysate line downstream of the fluid receptacle, and opening a second valve positioned along a fluid line fluidly coupling the spent dialysate line to the fluid receptacle.

In certain implementations, the method further includes after a predetermined amount of time has elapsed since opening the second valve, closing the second valve and opening the first valve.

In some implementations, the method further comprises displaying, on a display device of a dialysis machine of the dialysis system, the level of the one or more waste products detected in the spent dialysate.

In certain implementations, the method further includes determining that a threshold level of the one or more waste products is present in the spent dialysate, and in response, causing a dialysis machine of the dialysis system to generate an audible alert or a visual alert.

In some implementations, the method further includes determining that a threshold level of the one or more waste products is present in the spent dialysate, and in response, causing a dialysis machine of the dialysis system to transmit the detected level of the one or more waste products to a remote computing device.

In certain implementations, the method further includes mixing the spent dialysate and the chemical reagent by operating a stir bar within the fluid receptacle, applying vibrations to the fluid receptacle, or applying ultrasound pulses to the fluid receptacle.

In some implementations, the chemical reagent includes a phosphate detection reagent, and detecting the level of one or more waste products present in the spent dialysate using the spectroscopy sensor includes detecting a level of phosphate in the spent dialysate.

In certain implementations, the chemical reagent includes an alizarin red solution, and detecting the level of one or more waste products present in the spent dialysate using the spectroscopy sensor includes detecting a level of calcium in the spent dialysate.

In some implementations, the chemical reagent includes a picric acid solution, and detecting the level of one or more waste products present in the spent dialysate using the spectroscopy sensor includes detecting a level of creatinine in the spent dialysate.

In certain implementations, the chemical reagent includes a solution including crown ether 4-aminobenzo-18-crown-6 and crown ether modified gold nanoparticles, and detecting the level of one or more waste products present in the spent dialysate using the spectroscopy sensor includes detecting a level of potassium in the spent dialysate.

In some implementations, the chemical reagent includes a Hg-EDTA solution, and detecting the level of one or more waste products present in the spent dialysate using the spectroscopy sensor includes detecting a level of chloride present in the spent dialysate.

In certain implementations, the dialysis system includes a hemodialysis machine and a dialyzer.

In some implementations, flowing the spent dialysate from the spent dialysate line into the fluid receptacle includes flowing the spent dialysate from the dialyzer, through the spent dialysate line, and into the fluid receptacle.

In certain implementations, a first portion of the spent dialysate flows into the fluid receptacle and a second portion of the spent dialysate flows to a drain coupled to the spent dialysate line.

In some implementations, the dialysis system includes a peritoneal dialysis machine and a dialysis fluid cassette configured to be coupled to the peritoneal dialysis machine.

In certain implementations, flowing the spent dialysate from the spent dialysate line of the dialysis machine into the fluid receptacle includes flowing the spent dialysate from the dialysis fluid cassette, through the spent dialysate line of the peritoneal dialysis machine, and into the fluid receptacle.

In some implementations, a first portion of the spent dialysate flows into the fluid receptacle and a second portion of the spent dialysate flows to a drain bag coupled to the spent dialysate line.

In certain implementations, at least a portion of the spent dialysate line is defined by the dialysis fluid cassette, the fluid receptacle is defined by the dialysis fluid cassette, and flowing the spent dialysate from the spent dialysate line into the fluid receptacle includes flowing spent dialysate within the dialysis fluid cassette into the fluid receptacle.

In some implementations, the fluid receptacle is a first fluid receptacle, the chemical reagent is a first chemical reagent, the emitter is a first emitter, the spectroscopy sensor is a first spectroscopy sensor, and the method further includes flowing a second portion of the spent dialysate from the spent dialysate line of the dialysis system into a second fluid receptacle fluidly coupled to the spent dialysate line downstream of the first fluid receptacle, reacting the spent dialysate with a second chemical reagent contained in the second fluid receptacle to generate a second reacted sample, emitting electromagnetic radiation through the second reacted sample using a second emitter, and detecting a level of one or more waste products present in the second portion of the spent dialysate using a second spectroscopy sensor positioned proximate the second fluid receptacle.

In certain implementations, the fluid receptacle is a first fluid receptacle, the chemical reagent is a first chemical reagent, and the method further includes decoupling the first fluid receptacle from the spent dialysate line, coupling a second fluid receptacle to the spent dialysate line of the dialysis system proximate the spectroscopy sensor and the emitter, flowing a second portion of spent dialysate from the spent dialysate line into the second fluid receptacle, reacting the spent dialysate with a second chemical reagent contained in the second fluid receptacle to generate a second reacted sample, emitting electromagnetic radiation through the second reacted sample in the fluid receptacle using the emitter, and detecting a level of one or more waste products present in the spent dialysate using the spectroscopy sensor.

In a further aspect, a dialysis system includes a dialysis machine, a spent dialysate line, and a spent dialysate testing system. The spent dialysate testing system includes a fluid receptacle configured to receive spent dialysate from the spent dialysate line, a chemical reagent contained within the fluid receptacle and configured to react with the spent dialysate in the fluid receptacle to form a reacted sample, an emitter positioned at a first end of the fluid receptacle and configured to emit electromagnetic radiation, a spectroscopy sensor positioned at a second end of the fluid receptacle opposite the emitter and configured to detect an electromagnetic spectrum, and a frangible connector positioned between the fluid receptacle and the spent dialysate line, wherein the dialysis machine is configured to break the frangible connector in response to the dialysis machine receiving user input through a user interface of the dialysis machine.

Implementations can include one or more of the following features in any combination.

In some implementations, the chemical reagent includes a phosphate detection reagent, and the spent dialysate testing system is configured to detect a level of phosphate in the spent dialysate In certain implementations, the chemical reagent includes an alizarin red solution, and the spent dialysate testing system is configured to detect a level of calcium in the spent dialysate.

In some implementations, the chemical reagent includes a picric acid solution, and the spent dialysate testing system is configured to detect a level of creatinine in the spent dialysate.

In certain implementations, the chemical reagent includes a solution including crown ether 4-aminobenzo-18-crown-6 and crown ether modified gold nanoparticles, and the spent dialysate testing system is configured to detect a level of potassium in the spent dialysate.

In some implementations, the chemical reagent includes a Hg-EDTA solution, and the spent dialysate testing system is configured to detect a level of chloride in the spent dialysate.

In certain implementations, the emitter includes a light emitting diode.

In some implementations, the emitter emits electromagnetic radiation in a range of 100 nanometers to 400 nanometers.

In certain implementations, the emitter emits electromagnetic radiation in a range of 400 nanometers to 700 nanometers.

In some implementations, the emitter emits electromagnetic radiation in a range of 700 nanometers to 1 millimeter.

In certain implementations, the fluid receptacle includes a transparent, rigid material.

In some implementations, the fluid receptacle has a volume in a range of 1 milliliter to 3.5 milliliters.

In certain implementations, a distance between the emitter and the spectroscopy sensor is about 1 centimeter.

In some implementations, the fluid receptacle includes a vent.

In certain implementations, the fluid receptacle is a first fluid receptacle, the chemical reagent is a first chemical reagent, the emitter is a first emitter, the spectroscopy sensor is a first spectroscopy sensor, the frangible connector is a first frangible connector, and the spent dialysate testing system further includes: a second fluid receptacle configured to receive spent dialysis fluid from the spent dialysate line, a second chemical reagent contained within the second fluid receptacle and configured to react with the spent dialysate in the second fluid receptacle to form a second reacted sample, a second emitter positioned at a first end of the second fluid receptacle, a second spectroscopy sensor positioned at a second end of the second fluid receptacle opposite the second emitter and configured to detect a level of one or more waste products in the spent dialysate, and a second frangible connector fluidly positioned between the second fluid receptacle and the spent dialysate line.

In some implementations, the fluid receptacle is a first fluid receptacle, the chemical reagent is a first chemical reagent, and the spent dialysate testing system further includes a second fluid receptacle containing a second chemical reagent, wherein the first fluid receptacle is configured to be replaced with the second fluid receptacle after a level of one or more waste products in the spent dialysate in the first fluid receptacle has been detected by the spent dialysate testing system.

In certain implementations, the dialysis machine is a hemodialysis machine.

In some implementations, the dialysis machine is a peritoneal dialysis machine.

Implementations can include one or more of the following advantages.

In some implementations, the spent dialysate testing system enables detection of the level of one or more waste products in spent dialysate generated during dialysis treatment in real time during the treatment. Further, the dialysis system can alert an operator of the system if the detected level of one or more waste products is above a threshold value indicating a risk to the patient's health and a need for medical intervention. In addition, in some implementations, the dialysis system can automatically stop treatment in response to determining that the detected levels of one or more waste products in the spent dialysate is above a threshold level that is indicative of a need for medical intervention.

In some implementations, the spent dialysate testing system includes one or more chemical reagents that can be reacted with the spent dialysate to form one or more chemical compounds that include chromophores that can be detected using cost-effective spectroscopy, such as ultraviolet (UV) spectroscopy, infrared spectroscopy, or florescence spectroscopy. By reacting the spent dialysate with one or more chemical reagents prior to spectroscopic analysis of the spent dialysate, a greater variety of waste products within the spent dialysate can be analyzed using real-time UV, infrared, or florescence spectroscopy. The results of these tests can provide key insights into the efficacy of a patient's dialysis therapy. For example, spent dialysate phosphorus tests could be used to improve the dialysis therapy to better remove phosphate and reduce or eliminate patient risk of hyperphosphatemia.

The details of one or more embodiments are set forth in the accompanying drawings and the description below. Other aspects, features, and advantages of the disclosure will be apparent from the description and drawings, and from the claims.

DETAILED DESCRIPTION

Figure 1A:
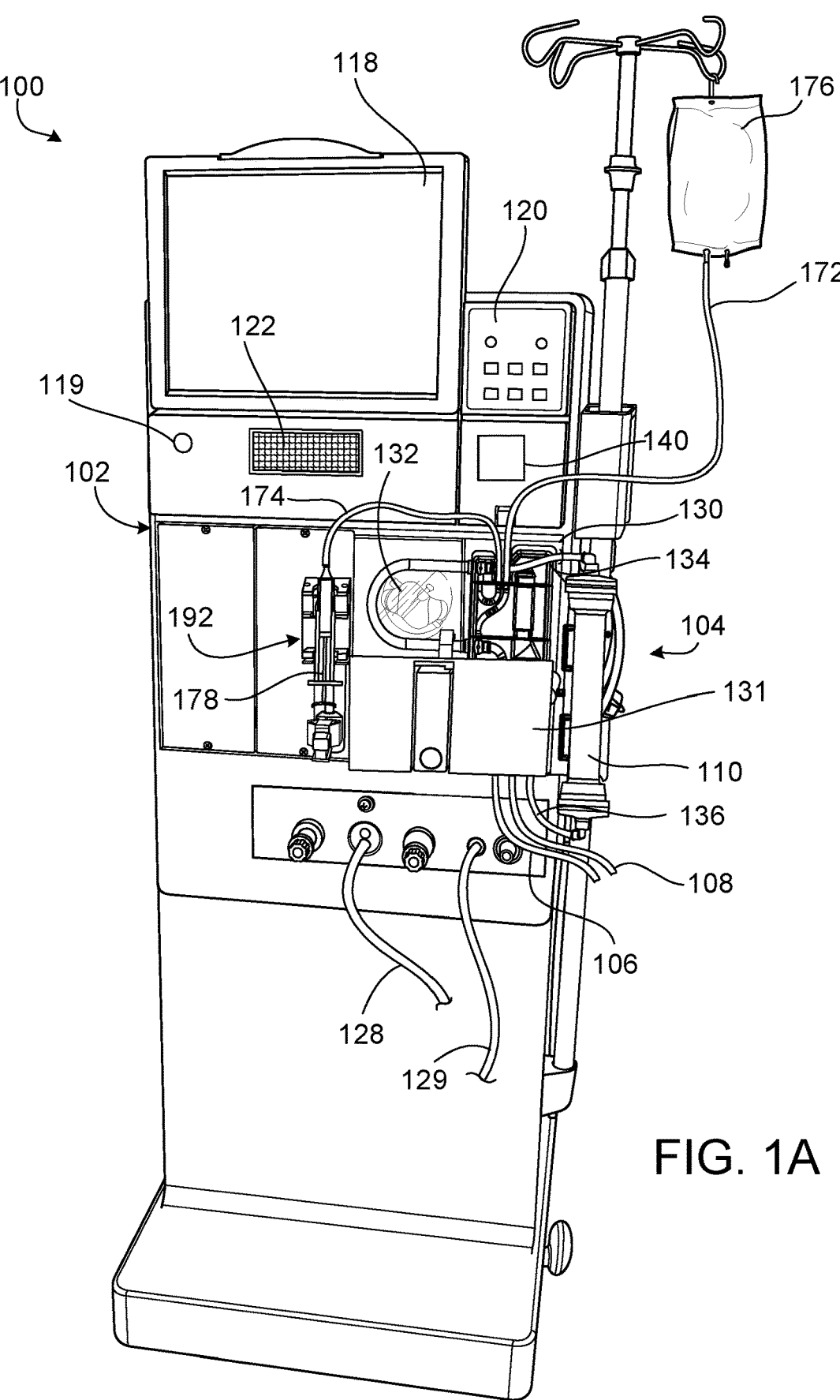
FIG. 1A is a perspective view of a hemodialysis treatment system.
Figure 1B:
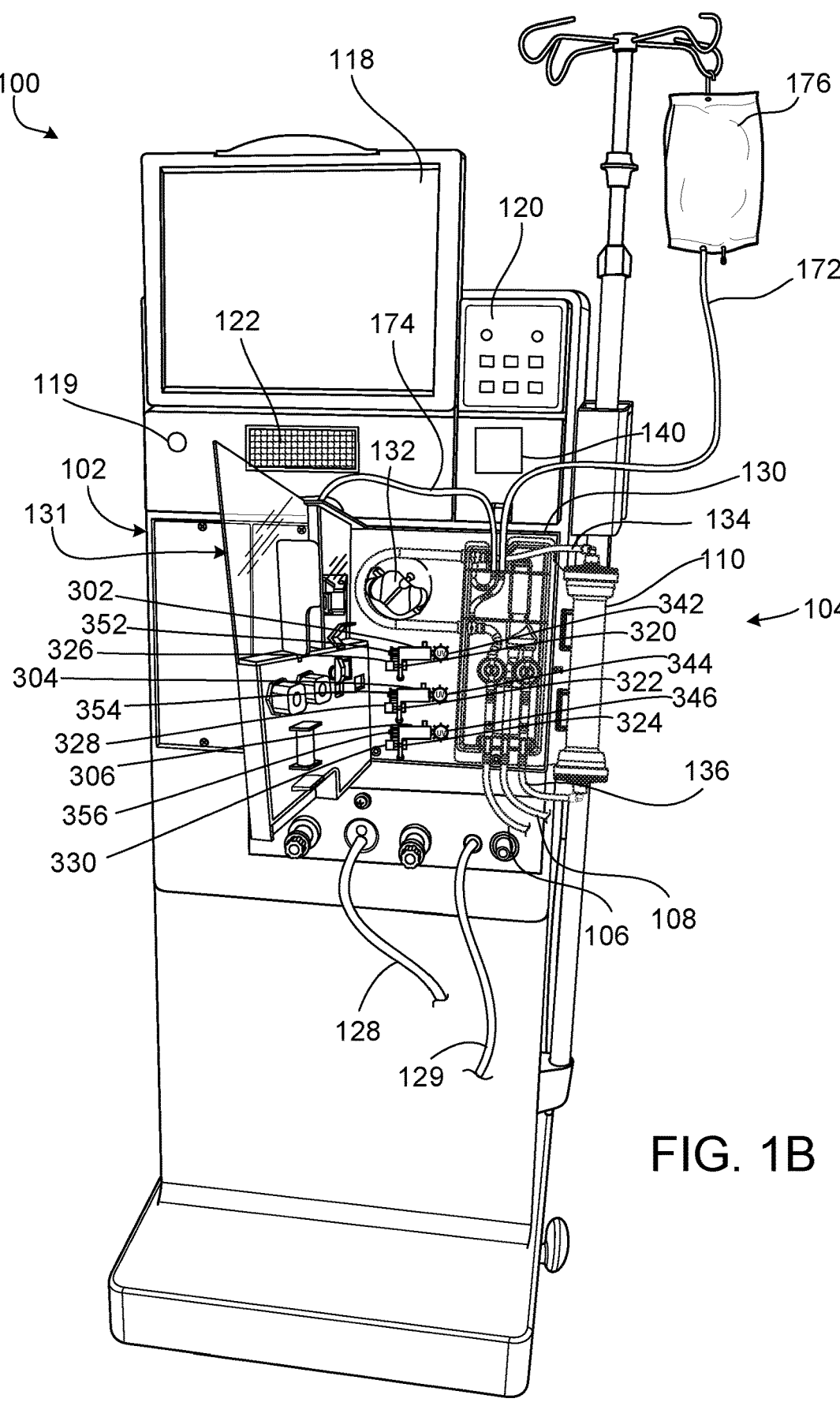
FIG. 1B is a perspective view of the hemodialysis treatment system of FIG. 1A with a door of a module of the hemodialysis system in an open position to expose a blood component set secured to the module.

Referring to FIGS. 1A and 1B, a hemodialysis system 100 includes a hemodialysis machine 102 to which a disposable blood component set 104 that forms a blood circuit is connected. During hemodialysis treatment, the arterial and venous patient lines 106, 108 of the blood component set 104 are connected to a patient and blood is circulated through various blood lines and components, including a dialyzer 110, of the blood component set 104.

At the same time, dialysate is circulated through a dialysate circuit formed by the dialyzer 110 and various other dialysate components and dialysate lines connected to the hemodialysis machine 102. Many of these dialysate components and dialysate lines are located inside the housing of the hemodialysis machine 102, and are thus not visible in FIGS. 1A and 1B. As described below and depicted in FIG. 2, the dialysate circuit 200 of the hemodialysis machine 102 includes a spent dialysate testing system 300 that can be used to detect a level of one or more waste products within spent dialysate generated during treatment. As will be described in further detail herein, the spent dialysate testing system 300 includes a set of cuvettes 302, 304, 306 for capturing samples of spent dialysate flowing through the dialysate circuit 200 and corresponding emitters 342, 344, 346 and spectroscopy sensors 352, 354, 356 for performing spectroscopic analysis of the spent dialysate collected in the cuvettes 302, 304, 306 in order to determine the level of one or more waste products within the spent dialysate.

During treatment, dialysate passes through the dialyzer 110 along with blood withdrawn from the patient. The blood and dialysate passing through the dialyzer 110 are separated from one another by a semi-permeable structure (e.g., a semi-permeable membrane and/or semi-permeable microtubes) of the dialyzer 110. As a result of this arrangement, waste products are removed from the patient's blood and collected in the dialysate. The filtered blood exiting the dialyzer 110 is returned to the patient (e.g., via the venous patient line 108). The dialysate that exits the dialyzer 110 includes waste products removed from the blood and is commonly referred to as "spent dialysate." The spent dialysate is routed from the dialyzer 110 to a drain via a spent dialysate line 136 and a drain line 128.

Still referring to FIGS. 1A and 1B, the dialysate circuit of the hemodialysis machine 102 is formed by multiple dialysate components and fluid lines positioned inside the housing of the hemodialysis machine 102 as well as the dialyzer 110, a fresh dialysate line 134, and a spent dialysate line 136. The fresh dialysate line 134 includes a connector adapted to connect to one end region of the dialyzer 110, and the spent dialysate line 136 includes a connector adapted to connect to another end region of the dialyzer 110.

As shown in FIGS. 1A and 1B, a drain line 128 and an ultrafiltration line 129 also extend from the hemodialysis machine 102. The drain line 128 and the ultrafiltration line 129 are fluidly connected to the various dialysate components and dialysate lines inside the housing of the hemodialysis machine 102 that form part of the dialysate circuit. During hemodialysis treatment, fresh dialysate is circulated through various dialysate lines and dialysate components, including the dialyzer 110, that form the dialysate circuit. As the dialysate passes through the dialyzer 110, it collects waste products and toxins from the patient's blood. The resulting spent dialysate is carried from the dialysate circuit to a drain via the drain line 128. When ultrafiltration is performed during treatment, a combination of the spent dialysate and excess fluid drawn from the patient is carried to the drain via the ultrafiltration line 129.

The blood component set 104 is secured to a module 130 attached to the front of the hemodialysis machine 102. The module 130 includes a blood pump 132 capable of driving blood through the blood circuit. The module 130 also includes various other instruments capable of monitoring the blood flowing through the blood circuit. The module 130 includes a door 131 that when closed, as shown in FIG. 1A, cooperates with the front face of the module 130 to form a compartment sized and shaped to receive the blood component set 104. In the closed position, the door 131 presses certain blood components of the blood component set 104 against corresponding instruments exposed on the front face of the module 130. This arrangement facilitates control of the flow of blood through the blood circuit and monitoring of the blood flowing through the blood circuit.

Still referring to FIGS. 1A and 1B, in addition to the blood lines 106, 108 forming the main blood circuit, a saline delivery line 172 and a drug delivery line 174 are connected to the blood circuit for introducing saline and drugs (e.g., heparin), respectively, into the blood circuit. The saline delivery line 172 is connected to a saline bag 176. The drug delivery line 174 is connected to a syringe 178 that contains a drug. A drug pump 192 also extends from the front of the hemodialysis machine 102. The drug pump 192 is a syringe pump that includes a clamping mechanism configured to retain the syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via the drug delivery line 174 during use, or to draw liquid from the blood circuit into the syringe 178 via the drug delivery line 174 during use.

The blood lines 106, 108, the saline delivery line 172, and the drug delivery line 174 can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate. The various blood lines 106, 108, the saline delivery line 172, and the drug delivery line 174 are typically retained within recessed channels formed in the hemodialysis machine 102. The recessed channels can have a diameter equal to or slightly less than the diameters of the lines 106, 108, 172, 174 so that the lines 106, 108, 172, 174 are retained within the channels with a friction fit. Alternatively or additionally, any of various other techniques can be used to secure the lines 106, 108, 172, 174 to the hemodialysis machine 102. For example, mechanical attachment devices (e.g., clips or clamps) can be used to retain the lines 106, 108, 172, 174.

Still referring to FIGS. 1A and 1B, the hemodialysis machine 102 also includes a touch screen 118 and a control panel 120. The touch screen 118 and the control panel 120 allow the operator to input various different treatment parameters to the hemodialysis machine 102 and to otherwise control the hemodialysis machine 102. In addition, the touch screen 118 serves as a display to convey information to the operator of the hemodialysis system 100. A speaker 122 is positioned below the touch screen 118 and functions to provide audio signals to the operator of the system 100. Thus, the hemodialysis machine 102 is capable of providing both visual alerts via the touch screen 118 and audio alerts via the speaker 122 to the operator of the system 100 during use.

Figure 2:
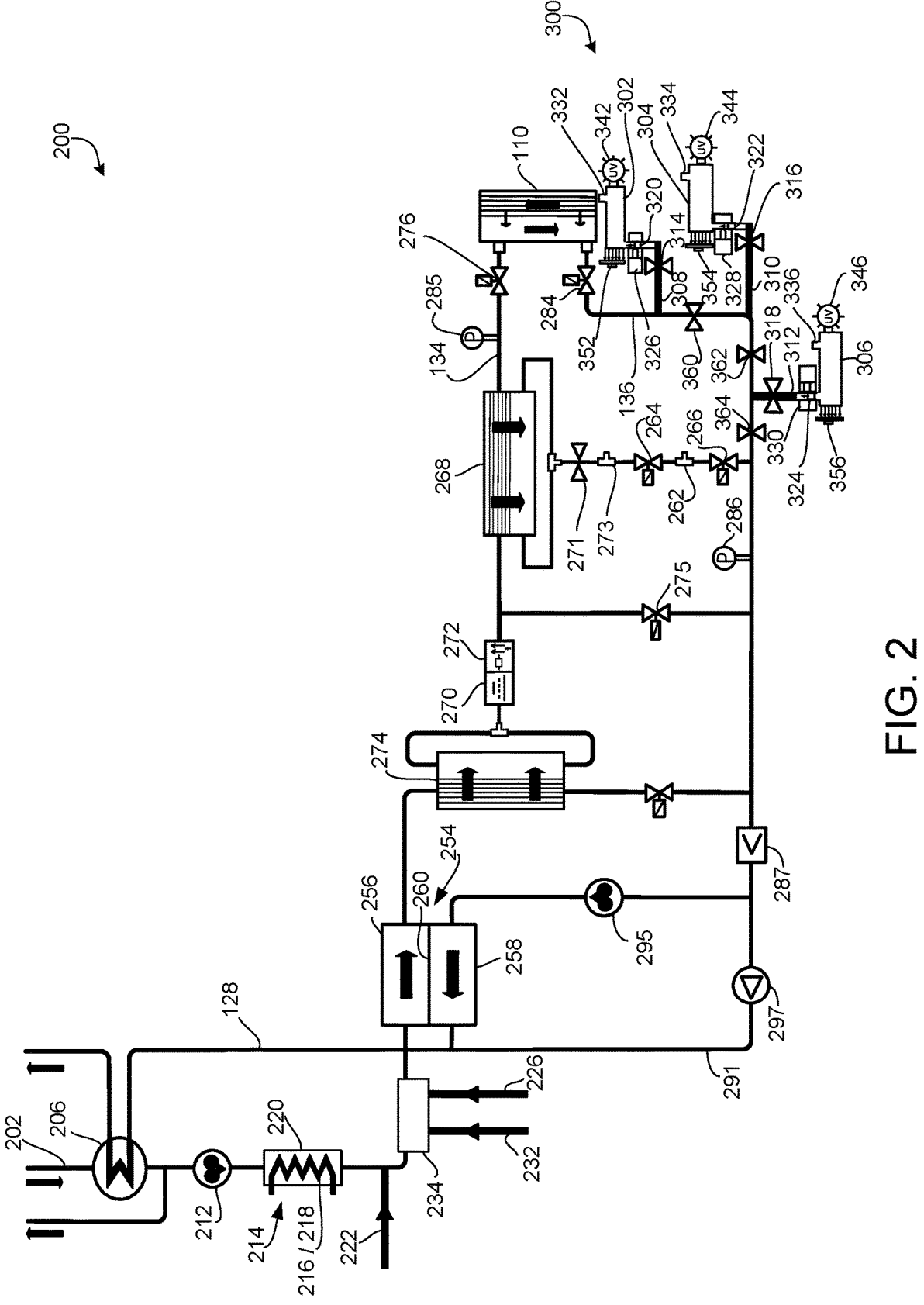
FIG. 2 is a schematic of a dialysate circuit of the hemodialysis system of FIGS. 1A and 1B with a spent dialysate testing system coupled to the dialysate circuit.

As previously discussed, the dialysate circuit of the hemodialysis machine 102 of FIGS. 1A and 1B is formed by multiple dialysate components and fluid lines positioned inside the housing of the hemodialysis machine 102 as well as the dialyzer 110, the fresh dialysate line 134, and the spent dialysate line 136. FIG. 2 is a schematic showing the flow paths of fluids into, through, and out of the dialysate circuit 200 of the hemodialysis machine 102.

The dialysate circuit 200 includes a number of dialysate components that are fluidly connected to one another via a series of fluid lines and the drain line 128. A water inlet 202 of the dialysate circuit 200 is configured to receive water from an external source and provide the water to a heat exchanger 206 via the water inlet 202. The heat exchanger 206 is configured to warm the water received by the dialysate circuit 200 through the water inlet 202 using the heat of spent dialysate (or other fluid) flowing on an opposite side of the heat exchanger 206.

After exiting the heat exchanger 206, the warmed water is flowed through a deaeration and heating chamber 214 by a deaeration pump 212. The deaeration and heating chamber 214 is configured to heat and deaerate water received by the dialysate circuit 200 through water inlet 202. The deaeration and heating chamber 214 includes a heater 216 to increase the temperature of the water received by the deaeration and heating chamber 214. For example, if the temperature of the water received by the deaeration and heating chamber 214 is below a threshold temperature, as detected by a temperature control thermistor, the heater 216 can be used to heat the water above the threshold temperature. The heater 216 includes a long heater rod 218 disposed within a housing 220 of the deaeration and heating chamber 214. As water flows through a passage formed between the heater rod 218 and the housing 220 of the deaeration and heating chamber 214 is warmed by the heater rod 218.

The warmed and deaerated water flows from the deaeration and heating chamber 214 to a mixing chamber 234 where the water is mixed with acid concentrate and bicarbonate concentrate to form dialysate. As can be seen in FIG. 2, the dialysate circuit 200 includes an acid concentrate inlet 226 coupled to a source of acid concentrate. In some implementations, an acid concentrate pump is configured to pump acid concentrate from the source of acid concentrate, through the acid concentrate inlet 226, and into the flow of water traveling through the mixing chamber 234. The dialysate circuit 200 also includes a bicarbonate concentrate inlet 232 that is coupled to a source of bicarbonate. In some implementations, a bicarbonate pump is configured to pump bicarbonate from the source bicarbonate, through the bicarbonate concentrate inlet 232, and into the flow of water traveling through the mixing chamber 234. Acid concentrate and bicarbonate concentrate flowing into the mixing chamber 234 via the acid concentrate inlet 226 and the bicarbonate concentrate inlet 232 mix with the water in the mixing chamber 234 to form fresh dialysate.

The dialysate exits the mixing chamber 234 and is drawn into a balancing device 254 fluidly connected to a fluid line downstream of the mixing chamber 234. The balancing device 254 is divided by a flexible membrane 260 into a first chamber half 256 and a second chamber half 258. As fluid flows into the first chamber half 256, fluid is forced out of the second chamber half 258, and vice versa. For example, as spent dialysate flows into the second chamber half 258 of balancing device 254, fresh dialysate is forced to flow out of first chamber half 256 of balancing device 254 towards the dialyzer 110. Similarly, as fresh dialysate flows into first chamber half 256 of balancing device 254, spent dialysate is forced to flow out of the second chamber half 258 of balancing device 254 towards the drain. This balancing device construction and alternating flow of fresh and spent dialysate helps to ensure that the volume of fresh dialysate entering the dialysate circuit 200 is equal to the volume of spent dialysate exiting the dialysate circuit 200 during treatment.

During treatment, fresh dialysate passing through the first chamber half 256 of the balancing device 254 is directed through a dialysate filter 274, which is configured to filter the fresh dialysate received from the balancing device 254. One example of such a dialysate filter 274 is the DIASAFE® plus dialysis fluid filter available from Fresenius Medical Care. During hemodialysis, a bypass valve 275 is closed and a dialyzer inlet valve 276 is open in order to direct the flow of dialysate from the dialysate filter 274 towards the dialyzer 110.

Following filtration of the fresh dialysate by the dialysate filter 274, the fresh dialysate flows through a conductivity cell 270 and a temperature monitor thermistor 272 downstream of the of the dialysate filter 274. The conductivity cell 270 and temperature monitor thermistor 272 regulate the temperature of the fresh dialysate entering the dialysate filter 274 and the dialyzer 110.

After following through the conductivity cell 270 and a temperature monitor thermistor 272, a portion of the fresh dialysate is directed to the dialyzer 110 through a second dialysate filter 268. The second dialysate filter 268 is the same as the first dialysate filter 274 and is configured to filter a portion of the fresh dialysate to generate substitution fluid. One example of such a dialysate filter 268 is the DIASAFE® plus dialysis fluid filter available from Fresenius Medical Care. During hemodialysis, a substituate valve 271 can be opened in order to allow fresh dialysate to be pulled across the second dialysate filter 268 to generate substitution fluid, which flows through a substituate port 273 connected to a substituate line.

When the dialyzer inlet valve 276 is in an open position and the substituate valve 271 is in a closed position, the dialysate fluid exits passes through the second dialysate filter 268 without being drawn across the filter membrane, and flows along a fresh dialysate line 134 towards the dialyzer 110. Before entering the dialyzer 110, the fresh dialysate flows through a pressure sensor 285 located along the fresh dialysate line 134. The pressure sensor 285 is configured to measure the pressure of the fresh dialysate entering the dialyzer 110 through the fresh dialysate line 134. Any of various different types of pressure sensors capable of measuring the pressure of the fresh dialysate passing into the dialyzer 110 can be used, such as ultrasonic sensors, piezoresistive strain gauges, capacitive sensors, electromagnetic sensors, or piezoelectric sensors.

After flowing through the dialyzer 110, spent dialysate exits the dialyzer 110 through the dialyzer outlet valve 284, and travels along a spent dialysate line 136 of the dialysate circuit 200. A pressure sensor 286 located along the spent dialysate line 136 is adapted to measure the pressure of the spent dialysate exiting the dialyzer 110. Any of various different types of pressure sensors capable of measuring the pressure of the spent dialysate passing from the dialyzer 110 can be used, such as ultrasonic sensors, piezoresistive strain gauges, capacitive sensors, electromagnetic sensors, or piezoelectric sensors.

A dialysate flow pump 295 is configured to pump the spent dialysate exiting the dialyzer 110 through a blood leak detector 287 that is configured to detect the presence of blood within the spent dialysate exiting the dialyzer 110. The blood leak detector 287 is an optical detector that includes a red/green light emitting diode (LED) and an optical receiver. As spent dialysate fluid flows through the blood leak detector 287, the LED of the blood leak detector 287 passes light through the fluid flowing through the blood leak detector 287 to the optical receiver of the blood leak detector 287. The presence of red blood cells in the spent dialysate can be detected by identifying a decrease in the amount of green light detected by the optical receiver of the blood leak detector 287 without the blood leak detector 287 also detecting a significant decrease in the amount of red light detected by the optical receiver.

Spent dialysate exiting the blood leak detector 287 is pumped through a fluid line to the second chamber half 258 of the balancing device 254 using the dialysate flow pump 295. As the second chamber half 258 of the balancing device 254 fills with the spent dialysate, fresh dialysate contained within the first chamber half 256 is expelled towards the dialyzer 110. Subsequently, as the first chamber half 256 of the balancing device 254 is refilled with fresh dialysate, the spent dialysate is forced out the second chamber half 258 of the balancing device 254 via drain line 128 to the drain.

As shown in FIG. 2, an ultrafiltration line 291 is connected the drain line 128 and fluidly coupled to the dialyzer 110. An ultrafiltration pump 297 is operatively connected to the ultrafiltration line 291 downstream of the dialyzer 110 such that when the ultrafiltration pump 297 is operated, spent dialysate can be directed to the drain via the ultrafiltration line 291. Operation of the ultrafiltration pump 297 while simultaneously operating the dialysate flow pump 295 causes increased vacuum pressure within the spent dialysate line 136, and thus creates increased vacuum pressure within the dialyzer 110. As a result of this increased vacuum pressure, additional fluid is pulled from the blood circuit into the dialysate circuit 200 across the semi-permeable structure of the dialyzer 110. Thus, the ultrafiltration pump 297 can be operated to remove excess fluid from the patient.

As depicted in FIG. 2, the dialysate circuit 200 also includes a disinfectant inlet 222 that can be used to introduce a disinfectant solution into the dialysate circuit 200. For example, a disinfectant fluid can be flowed through the dialysate circuit 200 via the disinfectant inlet 222 after each treatment in order to disinfect the dialysate circuit 200 following treatment.

The dialysate circuit 200 also includes a rinse port 262 and rinse valves 264, 266 that can be operated to prime and rinse the extracorporeal blood circuit. During priming or rinsing of the blood circuit, the arterial and venous patient lines 106, 108 can be fluidly connected to the rinse port 262 using a T-connector and the rinse valves 264, 266 can be opened to prime or rinse the blood lines 106, 108 with dialysate or substitution fluid generated by the dialysate circuit 200.

The various fluid lines and drain line 128 of the dialysate circuit 200 can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate.

Still referring to FIG. 2, as spent dialysate flows along the spent dialysate line 136, a portion of the spent dialysate flows into a spent dialysate testing system 300 positioned along the spent dialysate line. As will be described in detail herein, the spent dialysate testing system 300 is configured to test the spent dialysate for the presence of one or more waste products in the spent dialysate.

As can be seen in FIG. 2, the spent dialysate testing system 300 includes three cuvettes 302, 304, 306 fluidly connected to the spent dialysate line 136 by a respective fluid line 308, 310, 312. A fluid valve 314, 316, 318 is positioned along each fluid line 308, 310, 312 and is configured to control the flow of spent dialysate from the spent dialysate line 136 into each respective cuvette 302, 304, 306. Each of the cuvettes 302, 304, 306 is configured to receive a sample of spent dialysate flowing along the spent dialysate line 136 in order to perform testing on the spent dialysate.

The spent dialysate testing system 300 also includes three emitters 342, 344, 346 and three corresponding spectroscopy sensors 352, 354, 356. As can be seen in FIG. 1B, the emitters 342, 344, 346 and the corresponding spectroscopy sensors 352, 354, 356 are attached to the front face of the hemodialysis machine 102 (e.g., on module 130) and are covered by door 131 when closed. As shown in FIG. 2, when the cuvettes 302, 304, 306 are coupled to the hemodialysis machine 102, the emitter 342, 344, 346 is positioned at a first end of each cuvette 302, 304, 306 and the corresponding spectroscopy sensor 352, 354, 356 is positioned at a second, opposite end of the respective cuvette 302, 304, 306.

The emitters 342, 344, 346 each include one or more light emitting diodes (LEDs) that are configured to generate and emit a variety of electromagnetic waves, ranging from infrared, visible light, and ultraviolet (UV) light. For example, during testing of spent dialysate within the cuvettes 302, 304, 306, the emitters 342, 344, 346 each emit UV-vis light through the respective cuvette 302, 304, 306 along the length of the cuvette 302, 304, 306. In some implementations, the emitters 342, 344, 346 each include a Tungsten bulb. In some implementations, the emitters 342, 344, 346 include a broadband LED that can emit a wide range of electromagnetic waves.

The spectroscopy sensors 352, 354, 356 are each configured to measure the electromagnetic spectrum resulting from the emitters 243, 244, 246 passing UV-vis radiation through the fluid contained within the respective cuvette 302, 304, 306. As will be described in further detail herein, the electromagnetic spectrum detected by the spectroscopy sensors 352, 354, 356 can be used to identify the presence of one or more waste products present in the spent dialysate.

Each cuvette 302, 304, 306 is formed of a rigid material that defines a constant volume of space in order to allow for accurate spectroscopy testing of spent dialysate contained within the respective cuvette 302, 304, 306. In some implementations, the volume of each cuvette 302, 304, 306 is in a range of about 1 mL to about 3.5 mL. The length of each cuvette 302, 304, 306 corresponds to the distance between the respective emitter 342, 344, 346 and the respective spectroscopy sensor 352, 354, 356 and defines a path for light to pass from the respective emitter 342, 344, 346, through the solution within the cuvette 302, 304, 306, to the respective spectroscopy sensor 352, 354, 356. In some implementations, the length of the cuvette 302, 304, 306 defining the light path through the cuvette 302, 304, 306 is about 1 cm. The material forming each cuvette 302, 304, 306 is transparent to the required wavelengths of radiation, including infrared, visible, and UV radiation, thus allowing the radiation transmitted by the emitter 342, 344, 346 to pass through the cuvette 302, 304, 306 to the respective spectroscopy sensor 352, 354, 356. Possible materials for the cuvettes 302, 304, 306 include, but are not limited to, glass, PYREX® glass from Corning Inc., sapphire, optical-grade quartz, and suitable plastics, such as polyvinyl chloride (PVC), polymethyl methacrylate (PMMA), and polystyrene.

As will be described in further detail herein, each cuvette 302, 304, 306 contains a chemical reagent that is configured to react with a sample of spent dialysate that flows from the spent dialysate line 136 into the respective cuvette 302, 304, 306. The chemical reagent contained within each of the cuvettes 302, 304, 306 reacts with the spent dialysate to generate one or more chemical compounds that are indicative of the presence of waste products within the spent dialysate. These chemical compounds that are generated by reacting the spent dialysate with the chemical reagent contained with the cuvettes 302, 304, 306 a have chromophores that are detectable using low-cost spectroscopy methods, such as UV, infrared, or florescent spectroscopy, which allows for rapid analysis of the spent dialysate during treatment. In particular, the chemical reagent contained within the cuvettes 302, 304, 306 is a solution that enables detection of the concentration of phosphate within the spent dialysate by using low-cost spectroscopy techniques to detect a chromophore of the chemical compound formed by the reaction of the chemical reagent with the spent dialysate. In some implementations, the reagent contained within the cuvettes 302, 304, 306 to react with the spent dialysate to detect phosphate is PiColorLock™ Phosphate Detection Reagent available from Novus Biologicals.

Each cuvette 302, 304, 306 includes a vent 332, 334, 336 positioned along an upper surface of the cuvette 302, 304, 306 that is configured to release gas by-products generated by reacting the PiColorLock™ Phosphate Detection reagent with spent dialysate within the respective cuvette 302, 304, 306. The vents 332, 334, 336 prevent increased pressure within the cuvette 302, 304, 306 while the spent dialysate is reacting with the reagent contained in the cuvettes 302, 304, 306. Each vent 332, 334, 336 may contain a hydrophobic filter to prevent fluid from being released from the cuvette 302, 304, 306 through the vent 332, 334, 336. In addition, each vent 332, 334, 336 is sufficiently long to prevent a hazardous pressure build-up, even if the hydrophobic filter of the respective vent 332, 334, 336 is wetted.

Each cuvette 302, 304, 306 also includes a frangible connector 320, 322, 324 that separates the reagent contained within the respective cuvette 302, 304, 306 from the spent dialysate in the respective fluid line 308, 310, 312 until the respective frangible connector 320, 322, 324 is broken. The hemodialysis machine 102 includes corresponding mechanical frangible breaking mechanisms 326, 328, 330 and the cuvette 302, 304, 306 are attached the hemodialysis machine 102 such that the frangible connectors 320, 322, 324 are each positioned within a respective mechanical frangible breaking mechanism 326, 328, 330. For example, as depicted in FIG. 1B, the frangible breaking mechanisms 326, 328, 330 can be positioned on the front face of the hemodialysis machine 102 (e.g., on module 130) and the cuvettes 302, 304, 306 can be coupled to the module 130 of the hemodialysis machine 102 such that the frangible connector 320, 322, 324 of each cuvette 302, 304, 306 is positioned within the respective frangible breaking mechanism 326, 328, 330.

The mechanical frangible breaking mechanisms 326, 328, 330 are configured to crush or otherwise break the respective frangible connectors 320, 322, 324 in order to fluidly connect the respective cuvette 302, 304, 306 to the spent dialysate line 136. In some implementations, the frangible breaking mechanisms 326, 328, 330 each include a spring powered rod and a mechanical pin, and removal of the mechanical pin causes the spring powered rod of the respective frangible breaking mechanism 326, 328, 330 to push obliquely against the respective frangible connector 320, 322, 324. The mechanical pin of each of the frangible breaking mechanisms 326, 328, 330 can be removed either manually by the operator or through the actions of a stepper motor of the hemodialysis machine 102 in order to break the corresponding frangible connector 320, 322, 324. In some implementations, the frangible breaking mechanisms 326, 328, 330 apply rotational torque to the respective frangible connector 320, 322, 324 (e.g., using a stepper motor) in order to break the connectors 320, 322, 324.

The cuvettes 302, 304, 306 are configured to be disposable. For example, after performing a dialysis treatment in which spent dialysate is tested using the spent dialysate testing system 300, each of the cuvettes 302, 304, 306 can be disconnected from the hemodialysis machine 102 and discarded. New cuvettes can then be attached to the hemodialysis machine 102 via corresponding fluid lines 308, 310, 312 prior to performing another dialysis treatment or another test within the same dialysis treatment.

A method of performing hemodialysis treatment using the hemodialysis machine 102 will now be described with reference to FIGS. 1A, 1B, and 2.

Before the hemodialysis treatment is initiated, a human operator, e.g., a patient, a clinician, a nurse, or other clinical personnel, mounts the dialyzer 110 to the hemodialysis machine 102 and connects one end of each of the blood lines 106, 108 to the dialyzer 110. In some implementations, before performing dialysis treatment, the operator primes the blood circuit, including the blood lines 106, 108 and dialyzer 110, with saline from the saline bag 176.

Once the dialyzer 110 is connected to the hemodialysis machine 102, the blood lines 106, 108 are attached to the dialyzer 110, and the blood circuit has been primed, the operator connects the arterial line 106 to an arterial access of the patient (e.g., via a needle) and connects the venous line 108 to the venous access of the patient (via a needle). Once the blood lines 106, 108 are connected to the patient, hemodialysis treatment can be initiated. The patient or another operator of the hemodialysis machine 102 can, for example, use using a control on touch screen 118 or control panel 120 to initiate the hemodialysis treatment.

During the hemodialysis treatment, the blood pump 132 is operated to circulate blood through the dialyzer 110. A controller 140 of the hemodialysis machine 102 can be used to control the blood pump 132 through feedback control based on flow rates detected by one or more sensors of the hemodialysis machine 102. The blood pump 132 is driven such that blood in the arterial line 106 is drawn from the patient and directed toward the dialyzer 110 and through the venous line 108 back into the patient. The rotation of the blood pump 132 generates increased pressure within the dialyzer 110, which causes the blood within the dialyzer 110 to be pushed across the semipermeable membrane of the dialyzer 110.

As blood flows through the dialyzer 110, the dialysate flow pump 295 is operated to circulate dialysate through the dialyzer 110. Waste substances from the blood flowing through the dialyzer 110 diffuse into the dialysate, and the spent dialysate containing the waste products flows out of the dialyzer 110 along the spent dialysate line 136 towards the drain line 128. In addition, in some implementations, the ultrafiltration pump 497 is operated to draw excess fluid from the extracorporeal blood circuit into the dialysate circuit 200 to the drain line 128.

As spent dialysate flows along the spent dialysate line 136, the controller 140 of the hemodialysis machine 102 controls the spent dialysate testing system 300 to test the spent dialysate for the level of phosphate within the spent dialysate. A process of testing for the presence of phosphate within spent dialysate flowing through the dialysate circuit 200 using the spent dialysate testing system 300 will now be described with reference to FIGS. 1B and 2.

At the beginning of treatment, the fluid valves 314, 316, 318 along the fluid lines 308, 310, 312 are each closed and the fluid valves 360, 362, 364 along the spent dialysate line 136 are each open. As a result, at the beginning of treatment, spent dialysate flows freely through the spent dialysate line 136 and is prevented from flowing into the cuvettes 302, 304, 306. As treatment proceeds, spent dialysate flows from the dialyzer 110 through the dialysate circuit 200, including along the spent dialysate line 136 and through the drain line 128 towards a drain.

After a predetermined amount of time has elapsed from the start of treatment, the controller 140 causes the valve 360 positioned along the spent dialysate line 136 downstream of the cuvette 302 to close and the fluid valve 314 along the fluid line 308 to open. The controller 140 simultaneously causes the breaking mechanism 326 to break the frangible connector 320 in order to fluidly couple the cuvette 302 to the spent dialysate line 136. In some implementations, the controller 140 causes the valve 360 to close, the valve 314 to open, and the frangible breaking mechanism 326 to break the frangible connector 320 about 5 minutes to about 10 minutes after the start of treatment. In some implementations, the time at which the frangible breaking mechanism 326 to break the frangible connector 320 is determined based on the patient size or the treatment scheme. Once the valve 360 is closed, the valve 314 is open, and the frangible connector 320 is broken, spent dialysate flowing along the spent dialysate line 136 is directed into the cuvette 302. After a sufficient volume of spent dialysate is provided to the cuvette 302, the controller 140 causes the valve 314 along the fluid line 308 to close and the valve 360 to open, trapping the spent dialysate within the cuvette 302 and allowing the spent dialysate flowing along the spent dialysate line 136 to be directed towards the drain. In some implementations, the controller 140 causes the valve 314 to remain open and causes the valve 360 to remain closed for 1-2 cycles of the balancing device 254.

Once spent dialysate has been provided to the cuvette 302 and the valve 314 along the fluid line 308 is closed, the spent dialysate contained within the cuvette 302 mixes and interacts with the PiColorLock™ Phosphate Detection reagent contained within the cuvette 302. As the spent dialysate reacts with the reagent in the cuvette 302, any gases resulting from the reaction are released from the cuvette 302 through the vent 332. The spent dialysate reacts with the PiColorLock™ Phosphate Detection reagent in the cuvette 302 to form a compound that has a chromophore detectable using spectroscopy. This compound is green or yellow in color, and the concentration of the compound produced by reacting the reagent with the spent dialysate is proportional to the concentration of phosphate present in the spent dialysate.

Once the reaction between the spent dialysate and the reagent in the cuvette 302 is complete, the controller 140 controls the emitter 342 to transmit UV-vis radiation through the solution contained within the cuvette 302 towards the spectroscopy sensor 352 at a wavelength of about 625 nm. As the UV-vis radiation passes through the cuvette 302 and is absorbed and reflected by the solution contained within the cuvette 302, the resulting electromagnetic spectrum is detected by the spectroscopy sensor 352. The electromagnetic spectrum detected by the spectroscopy sensor 352 is transmitted to the controller 140 of the hemodialysis machine 102, and the controller 140 determines a level of phosphate present in the spent dialysate at the time of testing based on the electromagnetic spectrum detected by the spectroscopy sensor 352. In some implementations, the controller 140 causes the touch screen 118 of the hemodialysis machine 102 to display the detected phosphate level in real time.

Dialysis treatment continues while the spent dialysate is tested within the cuvette 302, and after a second amount of time has elapsed from the start of treatment (e.g., around the middle of treatment), the controller 140 causes a valve 362 positioned along the spent dialysate line 136 downstream of the cuvette 304 to close and the fluid valve 316 along the fluid line 310 to open. The controller 140 simultaneously causes the frangible breaking mechanism 328 to break the frangible connector 322 in order to fluidly couple the cuvette 304 to the spent dialysate line 136. In some implementations, the controller 140 causes the valve 362 to close, the valve 316 to open, and the frangible breaking mechanism 328 to break the frangible connector 322 about 90 minutes to about 100 minutes after the start of treatment. Once the valve 362 is closed, the valve 316 is open, and the frangible connector 322 is broken, spent dialysate flowing along the spent dialysate line 136 is directed into the cuvette 304.

After a sufficient volume of spent dialysate is provided to the cuvette 304, the controller 140 causes the valve 316 to close and the valve 362 to open, trapping the spent dialysate within the cuvette 304 and allowing the spent dialysate flowing along the spent dialysate line 136 to be directed towards the drain via the drain line 128. In some implementations, the controller 140 causes the valve 316 to close and causes the valve 362 to open for 1-2 cycles of the balancing device 254 after initially opening the valve 316 and closing the valve 362. The spent dialysate contained within the cuvette 304 mixes and interacts with the PiColorLock™ Phosphate Detection reagent solution contained within the cuvette 304 to form a compound that has a chromophore detectable using spectroscopy. As the spent dialysate reacts with the reagent solution in the cuvette 304, any gases resulting from the reaction are released from the cuvette 304 through vent 334.

Once the reaction between the spent dialysate and the reagent solution in the cuvette 304 is complete, the controller 140 controls the emitter 344 positioned proximate the cuvette 304 to transmit UV-vis radiation at a wavelength of about 625 nm through the solution contained within the cuvette 304 towards the spectroscopy sensor 354. As the UV-vis radiation passes through the cuvette 304 and is absorbed and reflected by the solution contained within the cuvette 304, the resulting electromagnetic spectrum is detected by the spectroscopy sensor 354 and is transmitted to the controller 140 of the hemodialysis machine 102. The controller 140 of the hemodialysis machine determines a level of phosphate present in the spent dialysate contained within the cuvette 304 based on the electromagnetic spectrum detected by the spectroscopy sensor 352. In some implementations, the controller 140 causes the touch screen 118 of the hemodialysis machine 102 to display the detected phosphate level in real time.

Dialysis treatment continues while the spent dialysate is tested within the cuvette 304, and as the end of the treatment approaches, the controller 140 causes a valve 364 positioned along the spent dialysate line 136 downstream of the cuvette 306 to close and the valve 318 to open. The controller 140 simultaneously causes the frangible breaking mechanism 330 to break the frangible connector 324 in order to fluidly couple the cuvette 306 to the spent dialysate line 136. In some implementations, the controller 140 causes the valve 364 to close, the valve 318 to open, and the frangible breaking mechanism 330 to break the frangible connector 324 about 180 minutes to about 190 minutes before the end of treatment. Once the valve 364 is closed, the valve 318 is open, and the frangible connector 324 is broken, spent dialysate flowing along the spent dialysate line 136 is directed into the cuvette 306.

After a sufficient volume of spent dialysate is provided to the cuvette 306, the controller 140 causes the valve 318 to close and the valve 364 to open, trapping the spent dialysate within the cuvette 306 and allowing the spent dialysate flowing along the spent dialysate line 136 to be directed towards the drain. In some implementations, the controller 140 causes the valve 318 to close and causes the valve 364 to open for 1-2 cycles of the balancing device 254s after initially opening the valve 318 and closing the valve 364. The spent dialysate contained within the cuvette 306 mixes and interacts with the PiColorLock™ Phosphate Detection reagent solution contained within the cuvette 306 to form a form a compound that has a chromophore detectable using spectroscopy. As the spent dialysate reacts with the reagent solution in the cuvette 306, any gases resulting from the reaction are released from the cuvette 306 through the vent 336.

Once the reaction between the spent dialysate and the reagent in the cuvette 306 is complete, the controller 140 controls the emitter 346 positioned proximate the cuvette 306 to transmit UV-vis radiation at a wavelength of about 625 nm through the solution contained within the cuvette 306 towards the spectroscopy sensor 356. As the UV-vis radiation passes through the cuvette 306 and is absorbed and reflected by the solution contained within the cuvette 306, the resulting electromagnetic spectrum is detected by the spectroscopy sensor 356 and is transmitted to the controller 140. The controller 140 determines a level of phosphate present in the spent dialysate contained within the cuvette 306 based on the electromagnetic spectrum detected by the spectroscopy sensor 356. In some implementations, the controller 140 causes the touch screen 118 of the hemodialysis machine 102 to display the detected phosphate level in real time.

In some implementations, if the level of phosphate by any one of the spectroscopy sensors 352, 354, 356 is above a threshold level (e.g., 6.5 mg/dL), the controller 140 causes the touch screen 118 to display a warning in real time indicating the detection of a high phosphate level in the spent dialysate. In some implementations, if the level of phosphate detected by any one of the spectroscopy sensors 352, 354, 356 is above a threshold level (e.g., 6.5 mg/dL), the controller 140 causes the speaker 122 of the hemodialysis machine 102 to emit a warning indicating a high phosphate level has been detected. In some implementations, if the detected level of phosphate is above a threshold level (e.g., 6.5 mg/dL), the controller 140 causes the hemodialysis machine 102 to alert the user to seek immediate medical intervention. In some implementations, if the detected level of phosphate is above a predetermined threshold, the controller 140 causes the hemodialysis machine 102 to provide the user with a recommendation (e.g., via the touch screen 118 and/or the speaker 122) to increase the frequency of dialysis treatment. In some implementations, if the detected level of phosphate is above a predetermined threshold, the controller 140 causes the hemodialysis machine 102 to transmit an alert to computing devices of one or more clinicians indicating the detected phosphate level In some implementations, one or more treatment parameters of the dialysate treatment are adjusted in response to detecting that the detected phosphate level in the spent dialysate exceeds a threshold level.

After treatment is completed, the cuvettes 302, 304, 306 are detached from the hemodialysis machine 102 and discarded. In addition, new, unused cuvettes can be coupled to the hemodialysis machine 102 in preparation for the next treatment to be performed using the hemodialysis machine 102.

In some implementations, mixing of the spent dialysate with the reagent contained in the cuvettes 302, 304, 306 is supplemented by mechanical means that agitate the solution contained within each cuvette 302, 304, 306 in order to enhance mixing of the solution in the cuvette 302, 304, 306 and, as a result, reduce the time required to react the spent dialysate with the reagent contained within the cuvette 302, 304, 306. For example, in some implementations, each cuvette 302, 304, 306 includes a magnetic stir bar and the hemodialysis machine 102 generates a magnetic field to rotate the stir bar to mix the solution contained within the cuvettes 302, 304, 306. For example, each cuvette 302, 304, 306 can contain a ceramic-coated bar magnet and the dialysis machine 102 can include a motor-powered rotating magnet that is positioned within the machine housing in proximity to the cuvettes. A magnetic field is generated by rotating the magnet within the housing of the hemodialysis machine 102, which causes the ceramic-coated bar magnets within the cuvettes 302, 304, 306 to rotate, which mixes the solution contained within the cuvettes 302, 304, 306. The motor rotating the magnet within the housing of the dialysis machine 102 can be controlled (e.g., using controller 140) to rotate the magnet in response to spent dialysate fluid being provided to a cuvette 302, 304, 306.

In some implementations, the hemodialysis machine 102 includes a mechanical vibrating mechanism that vibrates the cuvette 302, 304, 306 in order to enhance mixing of the solution within the cuvette 302, 304, 306. For example, as spent dialysate flows into a cuvette 302, 304, 306 and the corresponding valve 314, 316, 318 is closed, the controller 140 of the hemodialysis machine 102 can cause a vibrating mechanical mechanism of the hemodialysis machine 102 to vibrate and enhance mixing of the spent dialysate with the reagent contained within the respective cuvette 302, 304, 306. In some implementations, the dialysis machine 102 includes an oval-shaped electric motor head that is positioned on a face of the machine proximate the cuvettes 302, 304, 306 and is configured to rotate against the cuvette in order to enhance mixing of the spent dialysate with the reagent contained within the respective cuvette 302, 304, 306.

In some implementations, the hemodialysis machine 102 generates ultrasounds pulses directed at the cuvette 302, 304, 306 in order to enhance mixing of the solution within the cuvettes 302, 304, 306.

In some implementations, the hemodialysis machine 102 generates heat to enhance mixing of the spent dialysate provided to the cuvettes 302, 304, 306 with the reagent contained within the respective cuvette 302, 304, 306. For example, as spent dialysate flows into a cuvette 302, 304, 306 and the corresponding valve 314, 316, 318 is closed, the controller 140 controls a heating mechanism of the hemodialysis machine 102 to heat the fluid contained within the respective cuvette 302, 304, 306 to enhance mixing of the spent dialysate and reagent contained within the cuvette 302, 304, 306. Suitable heating mechanisms for heating the cuvettes 302, 304, 306 can include, but are not limited to, a quartz lamp, a quartz tube, a metal sheath, or ceramic heating elements that focus their thermal output on the cuvettes 302, 304, 306 from within the housing of the hemodialysis machine 102. In some implementations the hemodialysis machine 102 is configured to heat the solution of spent dialysate and reagent contained in the cuvettes 302, 304, 306 to a boiling point.

While certain embodiments have been described above, other embodiments are possible.

Figure 10:
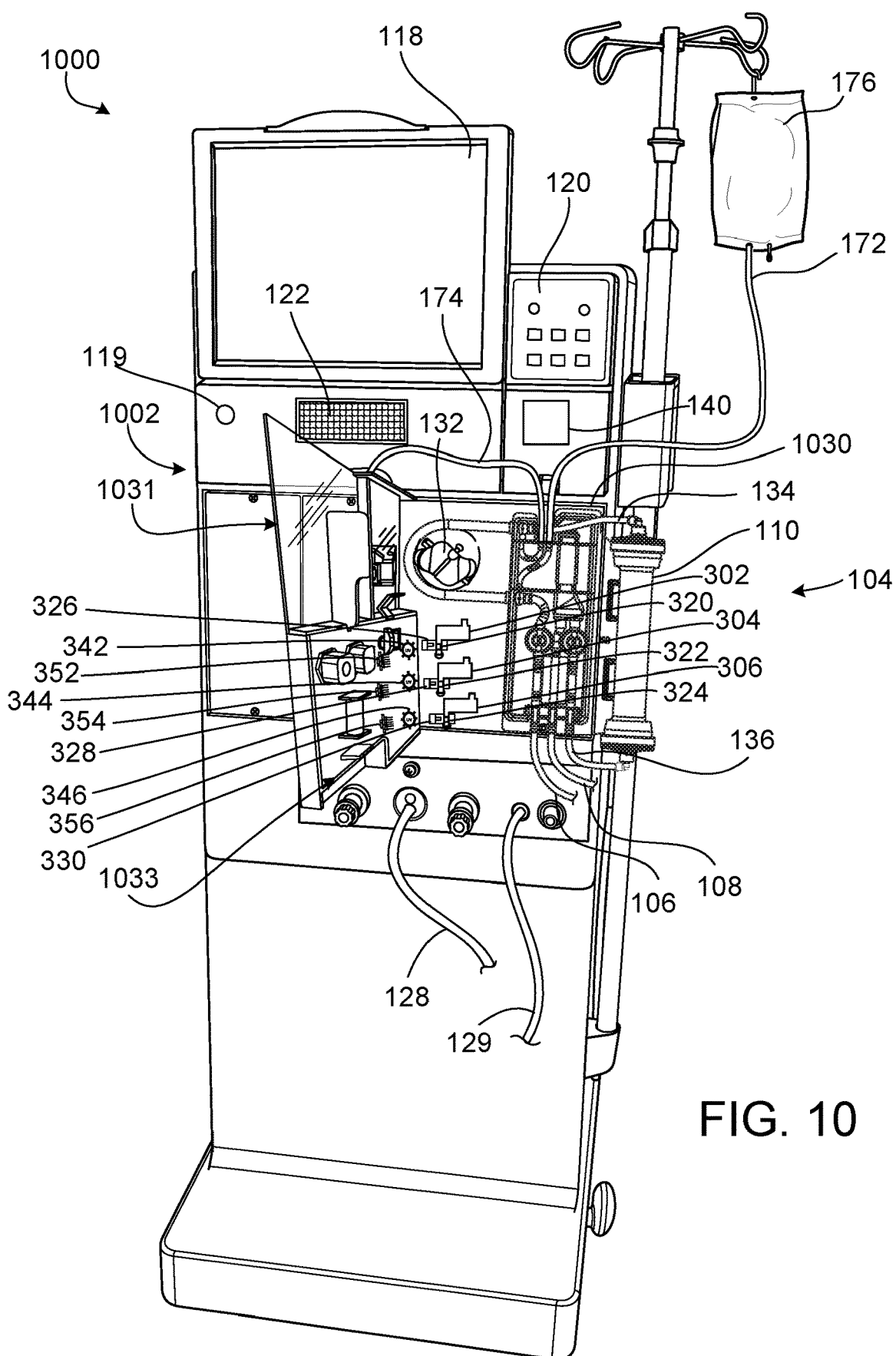
FIGS. 10 and 11 depict perspective views of alternate hemodialysis treatment systems.

For example, while the hemodialysis machine 102 has been described as including the emitters 342, 344, 346 and corresponding spectroscopy sensors 352, 354, 356 positioned on the module 130 on the face of the hemodialysis machine 102, other arrangements of the emitters 342, 344, 346 and spectroscopy sensors 352, 354, 356 on the hemodialysis machine 102 are possible. For example, as depicted in FIG. 10, in some implementations, the hemodialysis system 1000 includes emitters 342, 344, 346 and corresponding spectroscopy sensors 352, 354, 356 that are positioned on an interior surface 1033 of the door 1031 of the hemodialysis machine 102. The cuvettes 302, 304, 306 can be coupled to the module 1030, as depicted in FIG. 10, or to the door 1031 of the hemodialysis machine 102 such that the radiation generated by the respective emitter 342, 344, 346 can be transmitted through the cuvette 302, 304, 306 and the resulting spectrum can be detected by the corresponding spectroscopy sensor 352, 354, 356. For example, as depicted in FIG. 10, cuvettes 302, 304, 306 can be coupled to the module 1030 of the hemodialysis machine 102 such that when the door 1031 is closed an emitter 342, 344, 346 is positioned at a first end of each cuvette 302, 304, 306 and a corresponding spectroscopy sensor 352, 354, 356 is positioned at a second, opposite end of the respective cuvette 302, 304, 306.

Figure 11:
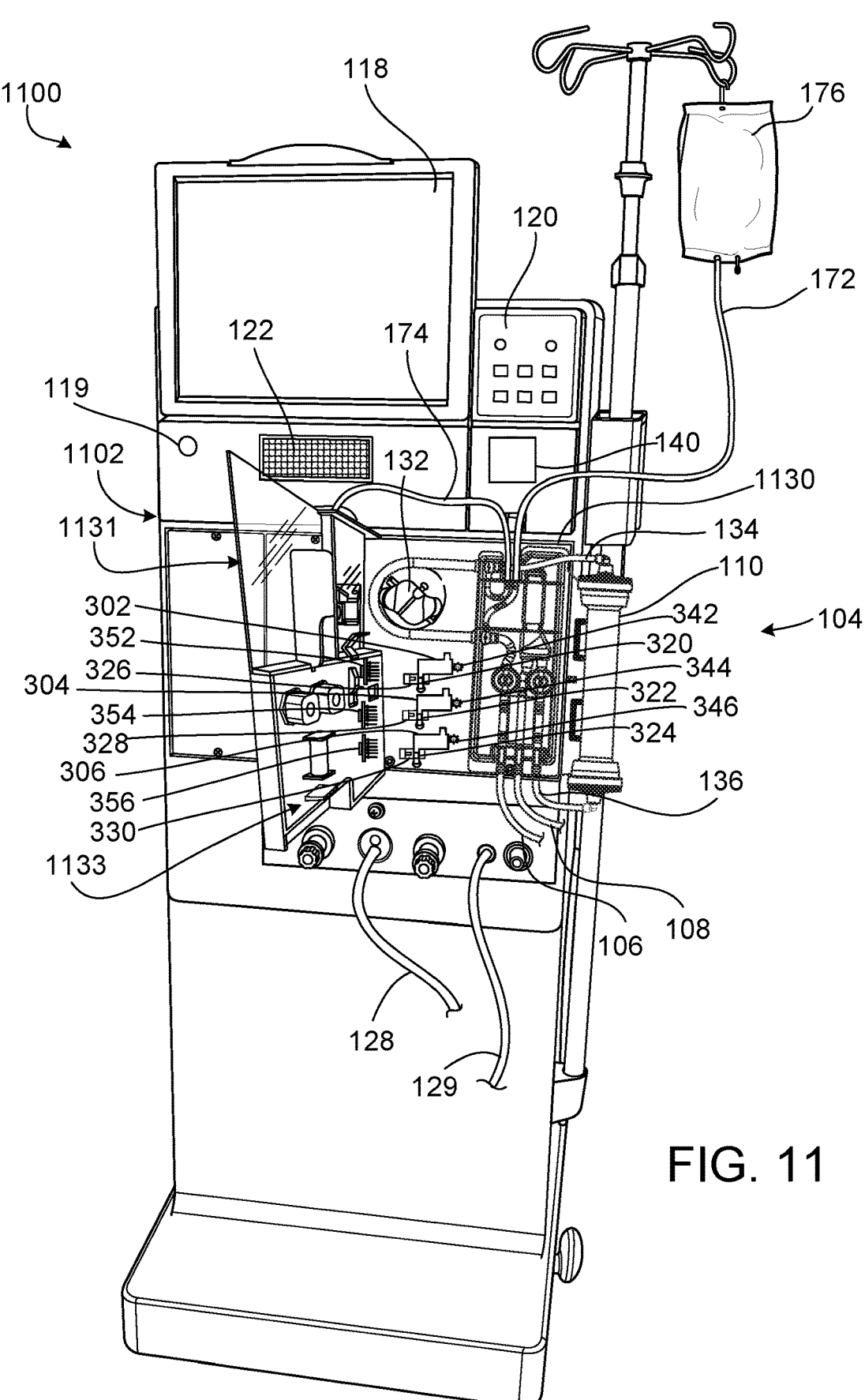

As can be seen in FIG. 11, in some implementations, the hemodialysis system 1100 includes emitters 342, 344, 346 that are attached to the front face of the hemodialysis machine 1102 (e.g., on module 1130) and corresponding spectroscopy sensors 352, 354, 356 that are positioned on an interior surface 1133 of the door 1131 of the hemodialysis machine 1102 opposite the respective emitters 342, 344, 346. The cuvettes 302, 304, 306 can be coupled to the hemodialysis machine 1102 such that when the door 1131 is closed each cuvette 302, 304 306 is aligned with a respective emitter 342, 344, 346 and spectroscopy sensors 352, 354, 356 such that the radiation can be transmitted through the cuvette 302, 304, 306 by the respective emitter 342, 344, 346 and the resulting spectrum can be detected by the corresponding spectroscopy sensor 352, 354, 356. For example, the cuvettes 302, 304, 306 can be attached to either the module 1130 of the hemodialysis machine 1102 (as depicted in FIG. 11) or the interior surface 1133 of the door 1131 of the hemodialysis machine 1102. In some implementations, the emitters 342, 344, 346 are attached on the interior surface 1133 of the door 1131 of the hemodialysis machine 1102 and the corresponding spectroscopy sensors 352, 354, 356 that are attached to the front face of the hemodialysis machine 1102 (e.g., on module 1130) opposite the respective emitters 342, 344, 346.

Figure 3:
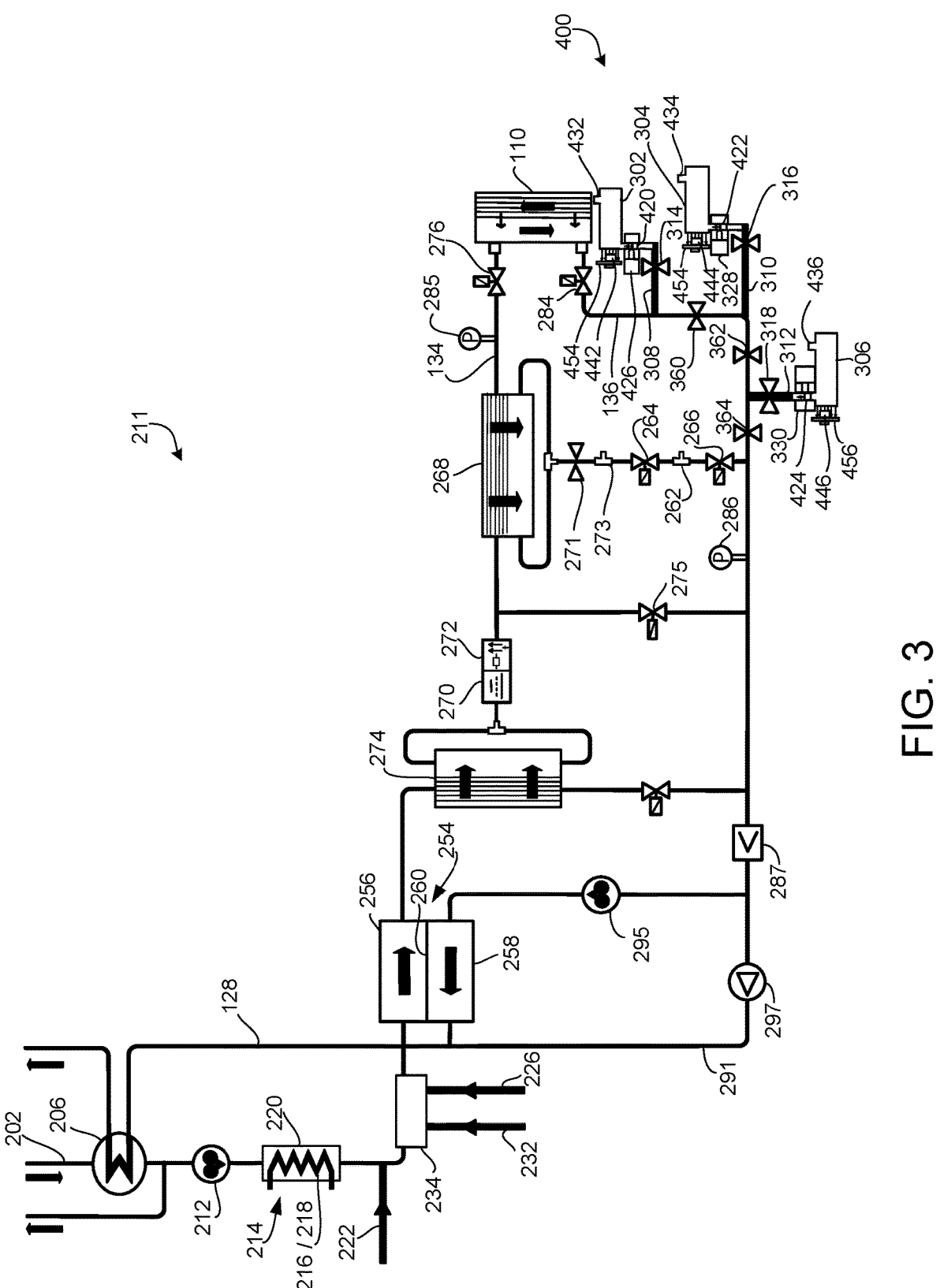
FIGS. 3-6 are schematics of alternate dialysate circuits for the hemodialysis system of FIGS. 1A and 1B with alternate spent dialysate testing systems coupled to the dialysate circuits.
Figure 12:
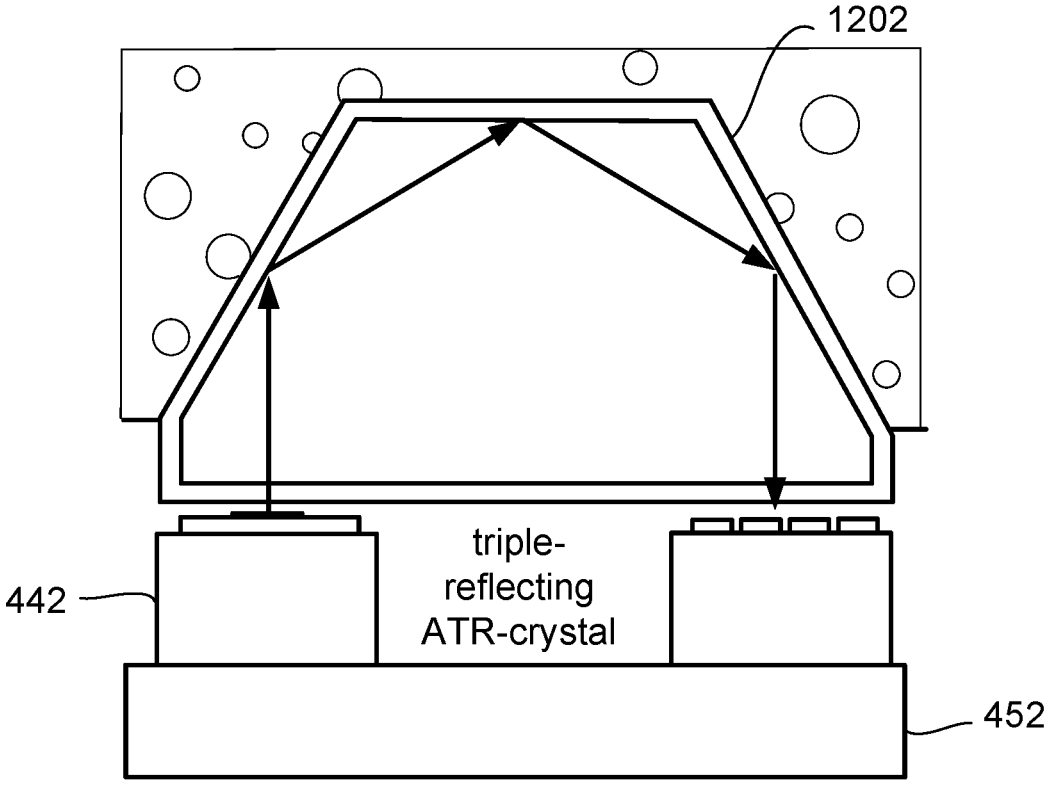
FIG. 12 depicts an example cuvette and spectroscopy sensor for the spent dialysate testing system of FIG. 3.

Further, while the spent dialysate testing system 300 is depicted in FIG. 2 as including emitters 342, 344, 346 and separate, corresponding spectroscopy sensors 352, 354, 356, in some implementation, a light source can be incorporated into each of the spectroscopy sensors of the spent dialysate system to perform spectroscopic analysis of the solution within the respective cuvette. For example, as depicted in FIG. 3, the spent dialysate testing system 400 includes three spectroscopy sensors 452, 454, 456 that each include an emitter 442, 444, 446 incorporated into each spectroscopy sensor 452, 454, 456. In order to perform spectroscopic analysis of the solution contained within a cuvette 302, 304, 306, the controller 140 of the hemodialysis machine 102 controls the emitter 442, 444, 446 of the spectroscopy sensor 452, 454, 456 positioned adjacent the cuvette 302, 304, 306 to emit light (e.g., UV, infrared, or fluorescent light) through the cuvette 302, 304, 306. As the light emitted by the emitter 442, 444, 446 is absorbed and reflected by the solution contained within the cuvette 302, 304, 306, the respective spectroscopy sensor 452, 454, 456 detects the resulting electromagnetic spectrum using the spectroscopy sensor 452, 454, 456. For example, as depicted in FIG. 12, in some implementations, the cuvettes 302, 304, 306 are formed of triple-reflecting crystal 1202 that reflects the light emitted by the respective emitter 442, 444, 446 throughout the solution contained within the respective cuvette 302, 304, 306 and back to a detector portion of the respective spectroscopy sensor 452, 454, 456. The electromagnetic spectrum detected by the spectroscopy sensor 452, 454, 456 can then be used to determine the level of one or more waste products (e.g., phosphate) within the spent dialysate contained within the respective cuvette 302, 304, 306. In some implementations, the emitters 442, 444, 446 are positioned perpendicular to the detector portion of the respective spectroscopy sensor 452, 454, 456.

While the spent dialysate testing system 300 has been described as sampling and testing the spent dialysate at times near the beginning of treatment, the middle of treatment, and the end of treatment, the spent dialysate testing system 300 can be controlled (e.g., using controller 140 of FIGS. 1A and 1B) to collect and test spent dialysate at other times during treatment.

Further, while controller 140 has been described as controlling the valves 360, 362, 364 and the spent dialysate testing system 300 to sample and test spent dialysate after predetermined time points during treatment, in some implementations, the valves 360, 362, 364 and the spent dialysate testing system 300 are controlled to collect and test spent dialysate samples based at least partly on feedback from one or more sensors.

Figure 4:
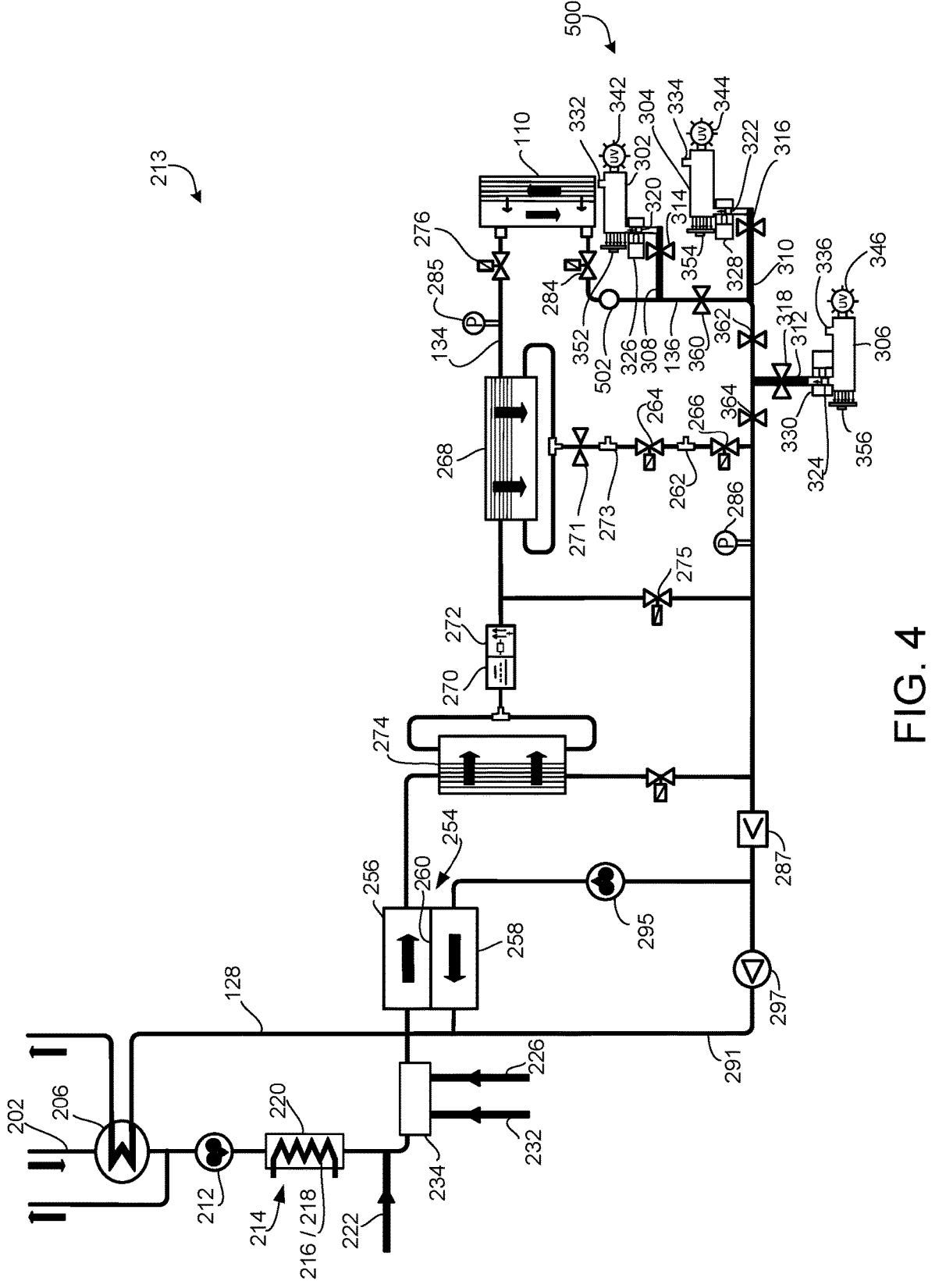

For example, as depicted in FIG. 4, in some implementations, the dialysate circuit 213 includes a flow sensor 502 positioned along the spent dialysate line 136. The flow sensor 502 measures the flow of spent dialysate along the spent dialysate line 136. The flow sensor 502 can include any suitable type of sensor for detecting flow, such as mechanical flow sensors, electromagnetic flow sensors, ultrasonic flow sensors, thermal mass flow sensors, audible flow sensors, or optical flow sensors. In some implementations, the flow sensor 502 is an audible flow sensor that includes a tube with a nozzle that permits a certain size drop of fluid to exit the tube, which produces a sound with each drop that can be detected by an audible detector and the frequency of the drops detected by the audible detector can be used to determine the flow rate of spent dialysate flowing along the spent dialysate line 136. Examples of a suitable flow sensor 502 include, but are not limited to, the Vortex flow sensor provided by SIKA® and a vertical flow sensor provided by Swagelok®.

The flow sensor 502 is communicably coupled to the controller 140 of the hemodialysis machine 102 to transmit signals to the controller 140 indicating the amount of fluid flow detected along the spent dialysate line 136. The controller 140 can then control the valves 360, 362, 364 and the spent dialysate testing system 300 to sample and test spent dialysate based on an amount of spent dialysis that has passed through the spent dialysate line 136, as determined based on signals received from the flow sensor 502. For example, as spent dialysate passes through spent dialysate line 136 during treatment, the flow sensor 502 monitors the amount of fluid flowing through the spent dialysate line 136 and sends signals in real time to the controller 140 indicating the amount of fluid passing through the spent dialysate line 136. Based on the signal received from the flow sensor 502, the controller 140 determines a total volume of spent dialysate that has passed through the spent dialysate line 136 during treatment. In response to detecting that the total amount of fluid that has passed through the spent dialysate line 136 during treatment has exceeded a first threshold amount, the controller 140 causes the valve 360 positioned along the spent dialysate line 136 downstream of the cuvette 302 to close and the valve 314 to open, and simultaneously causes the breaking mechanism 326 to break the frangible connector 320 in order to fluidly couple the cuvette 302 to the spent dialysate line 136 and direct spent dialysate into the cuvette 302. In some implementations, the controller 140 causes the valve 360 to close, the valve 314 to open, and the frangible breaking mechanism 326 to break the frangible connector 320 in response to determining that about 1000-8000 mL of spent dialysate has passed through the spent dialysate line 136.

Based on the signals received from the flow sensor 502, the controller 140 determines that an additional predetermined volume of spent dialysate has been provided to the spent dialysate line 136 since closing the valve 360 and opening the valve 314 and, in response, causes the valve 314 to close and the valve 360 to open, trapping the spent dialysate within the cuvette 302, and causes the emitter 342 to emit UV-vis radiation through the solution contained in the cuvette 302. In some implementations, the controller 140 causes the valve 314 to close, the valve 360 to open, and the emitter 342 to transmit UV-vis radiation in response to the flow sensor 502 detecting that an additional 5 mL of spent dialysate has been provided to the spent dialysate line 136 after opening the valve 314 and closing the valve 360. The level of phosphate present in the spent dialysate contained within the cuvette 302 can then be determined using the spectroscopy sensor 352, as described above with reference to FIG. 2.

Dialysis treatment continues while the spent dialysate is tested within the cuvette 302 and the flow sensor 502 continues to measure the flow through the spent dialysate line 136. In response to receiving a signal from the flow sensor 502 indicating that the total amount of fluid that has passed through spent dialysate line 136 during treatment has exceeded a second threshold amount greater than the first amount, the controller 140 causes the valve 362 positioned along the spent dialysate line 136 downstream of the cuvette 304 to close and the valve 316 to open, and simultaneously causes the frangible breaking mechanism 328 to break the frangible connector 322 in order to fluidly couple the cuvette 304 to the spent dialysate line 136 and direct spent dialysate into the cuvette 304. In some implementations, the controller 140 causes the valve 362 to close, the valve 316 to open, and the frangible breaking mechanism 328 to break the frangible connector 322 in response to determining that about 27 L to about 45 L of spent dialysate has passed through the spent dialysate line 136 since the beginning of treatment.

Based on the signals received from the flow sensor 502, the controller 140 determines that an additional predetermined volume of spent dialysate has been provided to the spent dialysate line 136 since closing the valve 362 and opening the valve 316 and, in response, causes the valve 316 to close and the valve 362 to open, trapping the spent dialysate within the cuvette 304, and causes the emitter 344 to emit Uv-vis radiation through the solution contained in the cuvette 304. In some implementations, the controller 140 causes valve 316 to close, the valve 362 to open, and the emitter 344 to transmit Uv-vis radiation in response to the flow sensor 502 detecting that an additional 5 mL of spent dialysate has been provided to the spent dialysate line 136 since opening the valve 316 and closing the valve 362. The level of phosphate present in the spent dialysate contained within the cuvette 304 can then be tested using the spectroscopy sensor 354, as described above with reference to FIG. 2.

Dialysis treatment continues while the spent dialysate is tested within the cuvette 304 and the flow sensor 502 continues to measure the flow through the spent dialysate line 136. In response to receiving a signal from the flow sensor 502 indicating that the total amount of fluid that has passed through the spent dialysate line 136 during treatment has exceeded a third threshold amount, the controller 140 causes the valve 364 positioned along the spent dialysate line 136 downstream of the cuvette 306 to close and the valve 318 to open, and simultaneously causes the frangible breaking mechanism 330 to break the frangible connector 324 in order to fluidly couple the cuvette 306 to the spent dialysate line 136 and direct spent dialysate into the cuvette 306. In some implementations, the controller 140 causes the valve 364 to close, the valve 318 to open, and the frangible breaking mechanism 330 to break the frangible connector 324 in response to determining that about 90 L of spent dialysate has passed through the spent dialysate line 136. The third threshold amount is greater than both the first and second threshold amounts. In some implementations, the third threshold amount corresponds to an amount that is slightly less than total amount of spent dialysate expected to be generated during the treatment.

Based on the signals received from the flow sensor 502, the controller 140 determines that an additional predetermined volume of spent dialysate has been provided to the spent dialysate line 136 since closing the valve 364 and opening the valve 318 and, in response, causes fluid the valve 318 to close and the valve 364 to open, trapping the spent dialysate within the cuvette 304, and causes the emitter 346 to emit Uv-vis radiation through the solution contained in the cuvette 306. In some implementations, the controller 140 causes the valve 318 to close, the valve 364 to open, and the emitter 346 to transmit UV radiation in response to the flow sensor 502 detecting that an additional 5 mL of spent dialysate has been provided to the spent dialysate line 136 since opening the valve 316 and closing the valve 364. The level of phosphate present in the spent dialysate contained within the cuvette 306 can then be tested using the spectroscopy sensor 356, as described above with reference to FIG. 2.

While the valves 314, 316, 318, 360, 362, 364 have been described as being controlled to allow 5 mL to be provided to each cuvette 302, 304, 306 based on signals received from the flow sensor 502, in some implementations, the amount of spent dialysate provided to the cuvette 302, 304, 306 is dependent on the size of the cuvette 302, 304, 306. For example, the amount of spent dialysate provided to each f the cuvettes 302, 304, 306 can range from about 0.1 mL to about 5 mL.

In addition, in some implementations, the valves 314, 316, 318, 360, 362, 364 are controlled based on both the volume of spent dialysate that has passed through the spent dialysate line 136 and an amount of time that has elapsed since the start of treatment. For example, in some implementations, in response to detecting that both the total amount of fluid that has passed through the spent dialysate line 136 during treatment has exceeded a first threshold amount based on signals received from flow sensor 502 and a first predetermined amount of time has elapsed since the beginning of treatment, the controller 140 causes the valve 360 positioned along the spent dialysate line 136 downstream of the cuvette 302 to close and the valve 314 to open, and simultaneously causes the breaking mechanism 326 to break the frangible connector 320 in order to fluidly couple the cuvette 302 to the spent dialysate line 136 and direct spent dialysate into the cuvette 302. Similarly, controller 140 can control the valve 362 to close and the valve 316 to open in response to determining that both the total amount of fluid that has passed through the spent dialysate line 136 during treatment has exceeded a second threshold amount greater than the first threshold amount and a second predetermined amount of time greater than the first predetermined amount of time has elapsed since the beginning of treatment. In addition, controller 140 can control the valve 364 to close and the valve 318 to open in response to determining that the total amount of fluid that has passed through the spent dialysate line 136 during treatment has exceeded a third threshold amount greater than both the first and second threshold amounts and that a third predetermined amount of time greater than the first and second predetermined amounts of time has elapsed since the beginning of treatment.

Figure 5:
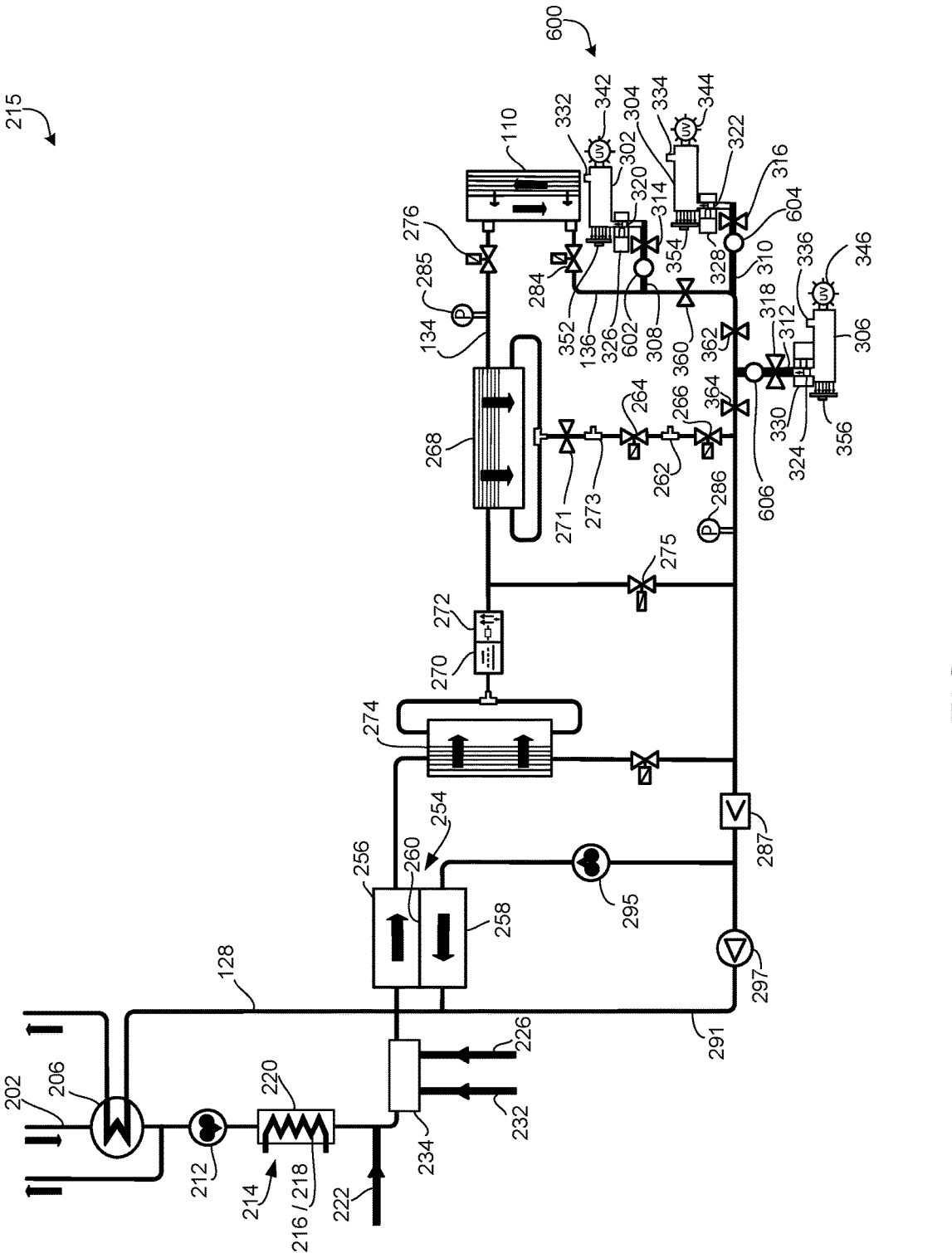

In some implementations, the fluid valves 314, 316, 318 are controlled to open and close based on a pressure detected within the respective fluid lines 308, 310, 312 coupled to the cuvettes 302, 304, 306. For example, as depicted in FIG. 5, the dialysate circuit 215 includes pressure sensors 602, 604, 606 positioned along each of fluid lines 308, 310, 312 fluidly coupling the cuvettes 302, 304, 306 to the spent dialysate line 136 downstream of the corresponding valves 314, 316, 318 along the fluid lines 308, 310, 312. Each of the pressure sensors 602, 604, 606 are configured to detect the pressure within the respective fluid lines 308, 310, 312 and are each communicably coupled to the controller 140 of the hemodialysis machine 102 to transmit signals to the controller 140 indicating the pressure along the respective fluid line 308, 310, 312. Any of various different types of pressure sensors capable of measuring the pressure of in the fluid lines 308, 310, 312 can be used, such as ultrasonic sensors, piezoresistive strain gauges, capacitive sensors, electromagnetic sensors, or piezoelectric sensors.

The controller 140 can control the valves 314, 316, 318 based on the pressure within the fluid line 308, 310, 312 detected by the respective pressure sensor 602, 604, 606. For example, during treatment, the controller 140 controls the valve 360 to close (e.g., after a predetermined amount of time has elapsed since the beginning of treatment or after a predetermined volume of dialysate fluid has passed through the spent dialysate line 128 since the beginning of treatment), which causes pressure to build within the fluid line 308 downstream of the valve 360 as spent dialysate flows into the fluid line 308. The pressure sensor 602 detects the increase in pressure along the fluid line 308 and transmits pressure measurements to the controller 140 in real time. Once the pressure detected along the fluid line 308 by the pressure sensor 602 exceeds a predetermined pressure threshold, the controller 140 causes the valve 314 along the fluid line 308 to open and causes the frangible breaking mechanism 326 to break the frangible connector 320 in order to fluidly connect the cuvette 302 to the spent dialysate line 136. As spent dialysate flows from the spent dialysate line 136 into the cuvette 302, the pressure within the fluid line 308 drops and then builds to a second predetermined pressure. Once the pressure detected along the fluid line 308 detected by the pressure sensor 602 exceeds the second predetermined pressure threshold, the controller 140 causes the valve 314 along the fluid line 308 to close, which contains the spent dialysate within the cuvette 302 for analysis of the spent dialysate within the cuvette 302. The level of phosphate present in the spent dialysate contained within the cuvette 302 can then be tested using the emitter 342 and the spectroscopy sensor 352, as described above with reference to FIG. 2.

The valves 316, 318 and the frangible breaking mechanisms 328, 330 can be similarly controlled based on the pressure detected along the fluid lines 310, 312 by the pressure sensors 604, 606 in order to control flow of spent dialysate into the respective cuvettes 304, 306. In addition, the controller 140 controls the valve 362 to open after a second predetermined amount of time greater than the first predetermined amount of time has elapsed since the beginning of treatment or a second predetermined volume of dialysate fluid greater than the first predetermined volume of fluid has passed through the spent dialysate line 136 since the beginning of treatment. Further, the controller 140 controls the valve 364 to open after a third predetermined amount of time greater than the first and second predetermined amounts of time has elapsed since the beginning of treatment or a third predetermined volume of dialysate fluid greater than the first and second predetermined volumes of fluid has passed through the spent dialysate line 136 since the beginning of treatment. As a result, the valves 360, 362, 364 are closed and the corresponding valves 314, 316, 318 are opened sequentially throughout the course of treatment to allow for sequential sampling and testing of the spent dialysate throughout treatment. In some implementations, the valves 360, 362, 364 are each closed in response to the controller 140 determining that both a respective predetermined amount of time has elapsed since the beginning of treatment and a respective predetermined volume of dialysate fluid has passed through the spent dialysate line 136 since the beginning of treatment.

In some implementations, the valves 360, 362, 364 along the spent dialysate line 136 and the spent dialysate testing system 300 are controlled to collect and test spent dialysate samples based input received from an operator of the hemodialysis machine 102. For example, during treatment, an operator of the hemodialysis machine 102 can use the touch screen 118 or the control panel 120 of the hemodialysis machine 102 to initiate a first test of the spent dialysate flowing through the spent dialysate line 136. In response to receiving operator input to initiate spent dialysate testing, the controller 140 operates the valve 360, the valve 314, and the frangible breaking mechanism 326 as described above to collect a sample of spent dialysate within the cuvette 302. Once a spent dialysate sample is collected in the cuvette 302 and reacted with the reagent contained in the cuvette 302, the controller 140 controls the emitter 342 to emit electromagnetic radiation through the cuvette 302 and, in response, receives a signal from the spectroscopy sensor 352 indicating the resulting spectrum detected by the spectroscopy sensor 352. The controller 140 determines the level of phosphate in the spent dialysate sample within the cuvette 302 and displays the determined level of phosphate on the touch screen 118 of the hemodialysis machine 102.

The operator can use the touch screen 118 or the control panel 120 to initiate two additional spent dialysate tests during treatment, which are performed within the cuvettes 304, 306 by controlling the valves 362, 364 and the valves 316, 318, respectively, to collect the samples within the cuvettes and controlling the emitters 344, 346 to emit electromagnetic radiation through the cuvettes 304, 306 and detecting the resulting electromagnetic spectrum using the spectroscopy sensors 354, 356, respectively. The operator can uses the touch screen 118 or the control panel 120 to initiate the testing of each of the three spent dialysate samples at any point during treatment.

While the spent dialysate testing system 300 has been depicted as including three cuvettes 302, 304, 306 for collecting and testing three samples of spent dialysate during treatment, other numbers of the cuvettes can be provided to collect and test other numbers of spent dialysate samples. In some examples, the spent dialysate testing system 300 includes a single cuvette and a single sample of spent dialysate is tested during treatment. In other examples, the spent dialysate testing system 300 includes two cuvettes and two samples of spent dialysate are tested during treatment. In some implementations, the system includes four or more cuvettes to collect and test a corresponding number of spent dialysate samples during treatment.

Figure 6:
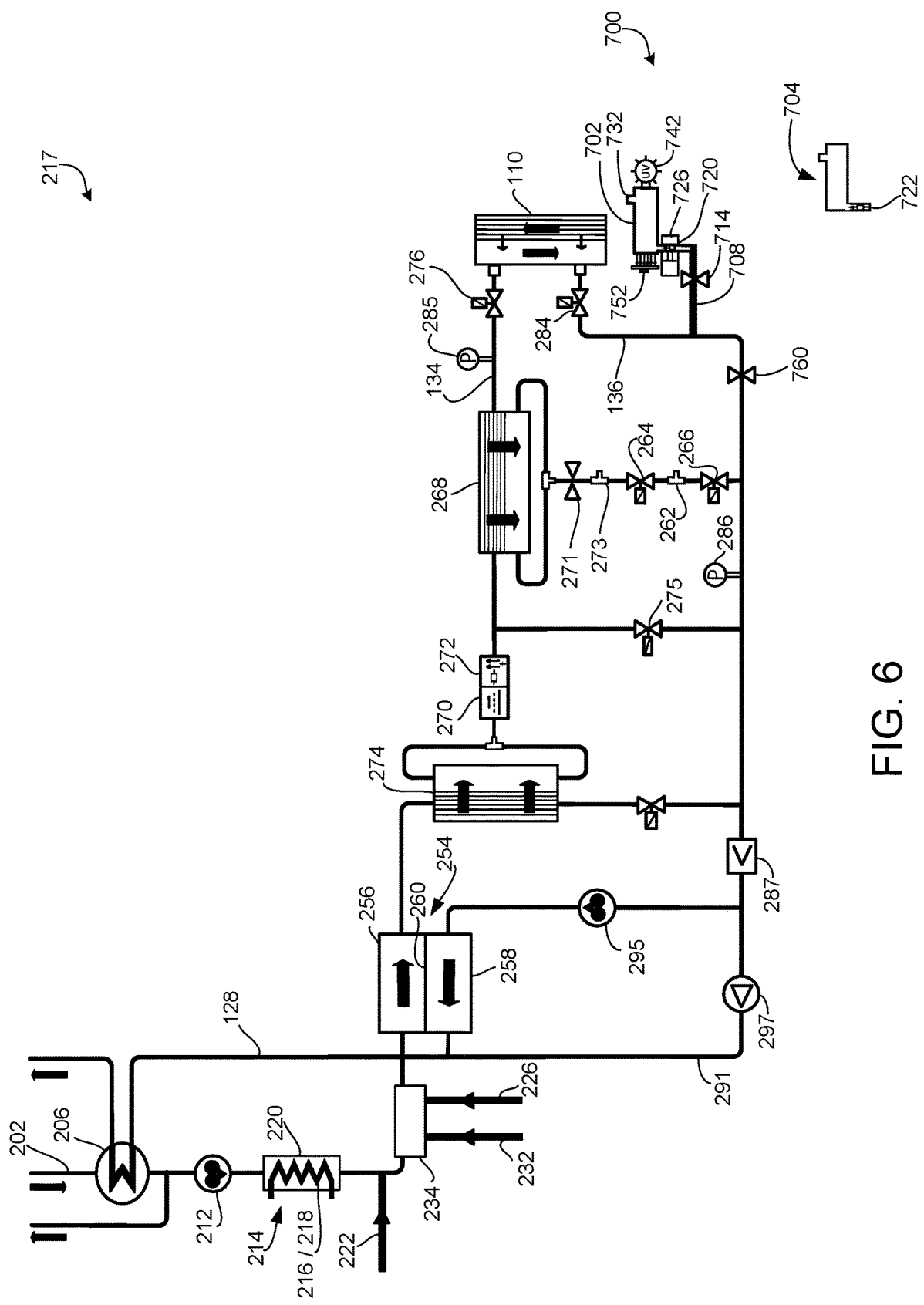

In addition, while the spent dialysate testing system 300 is depicted as including the same number of emitters 432, 434, 436 and spectroscopy sensors 352, 354, 356 as cuvettes 302, 304, 306 for sampling spent dialysate, in some implementation the testing system includes a single emitter and a single spectroscopy sensor for testing multiple cuvettes. For example, as depicted in FIG. 6, the spent dialysate testing system 700 includes a single emitter 732 and a corresponding spectroscopy sensor 752. The spent dialysate testing system 700 also includes a single corresponding mechanical frangible breaking mechanism 726. The dialysate circuit 217 also includes a fluid line 708 for fluidly coupling a cuvette 702 to the spent dialysate line 136 and a valve along the spent dialysate line 136 downstream of the fluid line 708.

Prior to beginning treatment, a disposable cuvette 702 is connected to the hemodialysis machine 102 to position the cuvette 702 between the emitter 742 and the spectroscopy sensor 752. In addition, a frangible connector 720 of the cuvette 702 is positioned within the frangible breaking mechanism 726. After a predetermined amount of time has elapsed from the start of treatment, the controller 140 causes the valve 760 positioned along the spent dialysate line 136 downstream of the fluid line 708 to close and the valve 714 to open. The controller 140 simultaneously causes the frangible breaking mechanism 726 to break the frangible connector 720 of the cuvette 702 in order to fluidly couple the cuvette 702 to the spent dialysate line 136. In some implementations, the controller 140 causes the valve 760 to close, the valve 714 to open, and the frangible breaking mechanism 726 to break the frangible connector 720 about 5 minutes to about 10 minutes after the start of treatment. Once the valve 760 is closed, the valve 714 is open, and the frangible connector 720 is broken, spent dialysate flowing along the spent dialysate line 136 is directed into the cuvette 702. After a sufficient volume of spent dialysate is provided to the cuvette 702, the controller 140 causes the valve 714 to close and the valve 760 to open, trapping the spent dialysate within the cuvette 702 and allowing the spent dialysate flowing along the spent dialysate line 136 to be directed towards the drain. In some implementations, the controller 140 causes the valve 714 to close and causes the valve 760 to open for 1-2 cycles of the balancing device 254 after initially opening the valve 714 and closing the valve 760.

Once spent dialysate has been provided to the cuvette 702 and the valve 714 is closed, the spent dialysate contained within the cuvette 702 reacts with a PiColorLock™ Phosphate Detection reagent contained in the cuvette 702 to form a compound that has a chromophore detectable using spectroscopy. The controller 140 simultaneously controls the emitter 742 to transmit Uv-vis radiation through the solution contained within the cuvette 702 towards the spectroscopy sensor 752. As the Uv-vis radiation is absorbed and reflected by the solution contained within the cuvette 702, the resulting electromagnetic spectrum is detected by the spectroscopy sensor 752. The resulting electromagnetic spectrum detected by the spectroscopy sensor 752 is transmitted to the controller 140, and the controller 140 determines a level of phosphate present in the spent dialysate contained within the cuvette 702 based on the electromagnetic spectrum detected by the spectroscopy sensor 752. In some implementations, the controller 140 causes the touch screen 118 to display the phosphate level detected in the spent dialysate in the cuvette 702 in real time.

After the level of phosphate within the spent dialysate sample in the cuvette 702 is determined, the controller 140 causes the hemodialysis machine 102 to generate a notification that the cuvette 702 needs to be replaced with a new cuvette. In some implementations, the notification indicating that the cuvette 702 needs to be replaced is a message displayed on the touch screen 118 of the hemodialysis machine 102. In some implementations, the notification indicating that the cuvette 702 needs to be replaced is an audio alert generated by speaker 122 of the hemodialysis machine 102. In some implementations, the hemodialysis machine 102 includes a light 119 that is illuminated to indicate that the cuvettes 702 needs to be replaced, and the controller 140 causes the light 119 to be illuminated after the level of phosphate within the spent dialysate sample in the cuvette 702 is determined. In some implementations, the controller 140 causes the light 119 to start flashing after the level of phosphate within the spent dialysate sample in the cuvette 702 is determined.

In response to the receiving the notification, an operator of the hemodialysis machine 102 can provide an input to the hemodialysis machine 102 (e.g., using the touch screen 118 or control panel 120 of the hemodialysis machine 102) indicating that the cuvette 702 will be replaced. In response to receiving the operator input, the controller 140 causes the hemodialysis machine 102 to pause treatment, which stops flow of spent dialysate along the spent dialysate line 136. While treatment is stopped, the operator of the hemodialysis machine 102 can remove the cuvette 702 filled with reacted solution from the hemodialysis machine 102 and dispose of the used cuvette 702. The operator then attaches a new, replacement cuvette 704 to fluid line 708, positioning the new cuvette 704 between the emitter 742 and the spectroscopy sensor 752.

Once the new cuvette 704 has been properly attached to hemodialysis machine 102, the operator can provide an input to the hemodialysis machine 102 (e.g., using the touch screen 118 or the control panel 120 of the hemodialysis machine 102) indicating that a new cuvette has been attached to the hemodialysis machine 102. In response to receiving the operator input, the controller 140 causes the hemodialysis machine 102 to resume treatment.

After a predetermined amount of time has elapsed since the new cuvette 704 was attached to the hemodialysis machine 102, the controller 140 causes the valve 760 to close and the valve 714 to open. The controller 140 simultaneously causes the frangible breaking mechanism 726 to break the frangible connector 722 of the cuvette 704 in order to fluidly couple the cuvette 704 to the spent dialysate line 136. In some implementations, the controller 140 causes the valve 362 to close, the valve 316 to open, and the frangible breaking mechanism 328 to break the frangible connector 322 about 5 minutes to about 10 minutes after receiving input indicating that the new cuvette 704 was attached to the hemodialysis machine 102. Once the valve 760 is closed, the valve 714 is open, and the frangible connector 722 is broken, spent dialysate flowing along the spent dialysate line 136 is directed into the cuvette 704. After a sufficient volume of spent dialysate is provided to the cuvette 704, the controller 140 causes the valve 714 to close and the valve 760 to open, trapping the spent dialysate within the cuvette 704 and allowing the spent dialysate flowing along the spent dialysate line 136 to be directed towards the drain via drain line 128. In some implementations, the controller 140 causes the valve 714 to close and causes the valve 760 to open for 1-2 cycles of the balancing chamber after initially opening the valve 714 and closing the valve 760.

Once spent dialysate has been provided to the cuvette 704 and the valve 714 is closed, the spent dialysate contained within the cuvette 704 reacts with the PiColorLock™ Phosphate Detection reagent in the cuvette 704 to form a compound that has a chromophore detectable using spectroscopy. The controller 140 simultaneously controls the emitter 742 to transmit Uv-vis radiation through the solution contained within the cuvette 704 towards the spectroscopy sensor 752. As Uv-vis radiation is absorbed and reflected by the solution contained within the cuvette 704, the resulting electromagnetic spectrum is detected by the spectroscopy sensor 752. The resulting electromagnetic spectrum detected by the spectroscopy sensor 752 is transmitted to the controller 140, and the controller 140 determines a level of phosphate present in the spent dialysate contained within the cuvette 704 based on the electromagnetic spectrum detected by spectroscopy sensor 752. In some implementations, the controller 140 causes the touch screen 118 of the hemodialysis machine 102 to display the phosphate level detected in the spent dialysate in the cuvette 704 in real time.

After treatment is completed, the cuvette 704 is detached from the hemodialysis machine 102 and discarded. In addition, a new, unused cuvette can be coupled to the hemodialysis machine 102 in preparation for the next treatment to be performed using the hemodialysis machine 102.

While the spent dialysate testing system 700 has been described as being used to collect and test two samples of spent dialysate during treatment, other numbers of replacement cuvettes can be provided to collect and test other numbers of spent dialysate samples during treatment. For example, two or more replacement cuvettes 704 can be used over the course of treatment to collect and test a corresponding number of spent dialysate samples, each replacement cuvette being discarded once testing using the respective cuvette is complete.

In addition, while the spent dialysate testing system 700 has been described as using operator input to determine whether a new, replacement cuvette 704 has been attached to hemodialysis machine 102, in some implementations, one or more sensors can be used in addition to or as an alternative to operator input in order to detect whether a new, replacement cuvette 704 has been attached to hemodialysis machine 102. For example, the hemodialysis machine 102 can include a switch on the front face of the module 130 adjacent to the cuvette 702, and the switch can be when a cuvette 702 is detached from the machine and a new, replacement cuvette 704 is attached to hemodialysis machine 102. The switch could be any suitable type of mechanical switch, such as a contact switch. In some implementations, the hemodialysis machine 102 includes a Hall effect sensor on the front face of the module 130 adjacent to the cuvette 702, and the Hall effect sensor interacts with a magnet contained within or attached to the cuvettes 702, 704 to detect when the first cuvette 702 is removed from the hemodialysis machine 102 and a new, replacement cuvette 704 has been attached to the hemodialysis machine 102.

In some implementations, the spectroscopy sensor 752 can be used to determine or confirm that a new, replacement cuvette has been attached to the hemodialysis machine 102. For example, after a predetermined amount of time has elapsed since testing the spent dialysate in the first cuvette 702 and before re-opening the valve 714, the emitter 742 can be controlled to emit light through the cuvette attached to the hemodialysis machine 102, and the spectroscopy sensor 752 can detect the resulting electromagnetic spectrum. If the used cuvette 702 is still attached to the hemodialysis machine 102, the spectroscopy sensor 752 will detect a resulting electromagnetic spectrum corresponding to the reacted solution, and based on this detection by the spectroscopy sensor 752, the controller 140 of the hemodialysis machine 102 will cause the hemodialysis machine 102 to generate an alarm (e.g., using the display 118 or speaker 122) to notify the operate to replace the used cuvette 702 with a new cuvette 704.

While the dialysate circuit 200 has been described as including an acid concentrate inlet 226 coupled to a source of acid concentrate for mixing with the deaerated and warmed water to form dialysate solution, in some implementations, the dialysate circuit 200 additionally or alternatively includes an inlet for receiving an electrolyte concentrate to be introduced into and mixed with the deaerated and warmed water in the mixing chamber 234 to form an electrolyte solution.

While the spent dialysate testing systems 300, 400, 500, 600, 700 have been described as controlling valves 314, 316, 318, 714, 360, 362, 364, 760 based on the cycles of the balancing chamber device 254 in order to fill the cuvettes 302, 304, 306, 702, 704, in some implementations, the dialysate circuit includes one or more servo pumps and one or more valves of the spent dialysate testing systems 300, 400, 500, 600, 700 are controlled to fill the cuvettes with spent dialysate based on a flow rate of the servo pumps. For example, a controller of a hemodialysis machine with a servo pump can control a first valve to close and control a second valve to open about 2 seconds to about 7 seconds after initially opening the first valve and closing the second valve in order to capture a sample of spent dialysate within the cuvette. In some implementations, the amount of time required to capture a sample of spent dialysate within the cuvette is dependent on the rate of the servo pump(s) of the hemodialysis machine. For example, the valves 314, 316, 318, 714, 360, 362, 364, 760 can controlled to capture spent dialysate within the respective cuvette 302, 304, 306, 702, 704 based on timing the opening and closing of the valves 314, 316, 318, 714, 360, 362, 364, 760 with the pump strokes of the servo pumps of the hemodialysis machine.

While the spent dialysate testing systems 300, 400, 500, 600, 700 have been described as being used as part of the hemodialysis system 100, the spent dialysate testing systems can also be used during other blood treatments including, hemofiltration (HF) treatment, hemodiafiltration (HDF) treatment, and peritoneal dialysis (PD) treatment.

Figure 7:
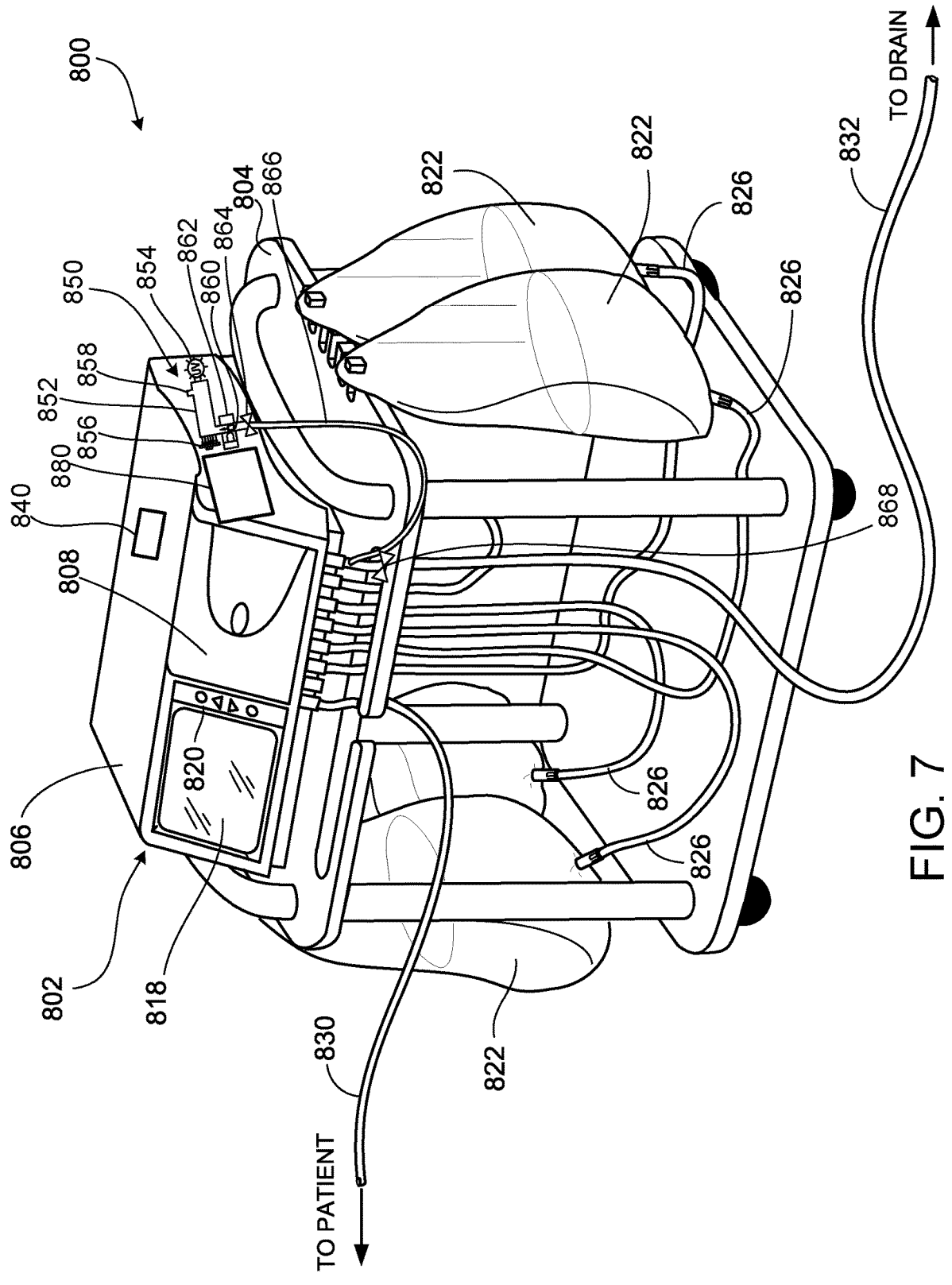
FIG. 7 is a perspective view of a peritoneal dialysis (PD) treatment system that includes a spent dialysate testing system.

FIG. 7 depicts an example peritoneal dialysis (PD) system 800 that can be used to perform PD treatment. A PD treatment typically begins by draining fluid from a patient's peritoneal cavity. Once the patient's peritoneal cavity has been drained, the patient's peritoneal cavity is filled with dialysate, which then dwells in the patient's peritoneal cavity for a period of time. After delivering the dialysate to the patient's peritoneal cavity and permitting the dialysate to dwell in the peritoneal cavity for a predetermined period of time, the dialysate is drained from the peritoneal cavity. The process of draining, filling, dwelling, and draining is repeated throughout a PD treatment cycle. Spent dialysate drained from the patient's peritoneal cavity during the draining phase of treatment can be collected in one or more drain bags or sent directly to a drain.

The PD system 800 includes a PD cycler 802 and a disposable set connected thereto that together can be used to perform automated peritoneal dialysis (APD) treatments. The PD cycler 802 is designed to automatically infuse, dwell, and drain dialysate to and from the patient's peritoneal cavity. An APD treatment typically lasts for several hours, often beginning with an initial drain cycle to empty the peritoneal cavity of used or spent dialysate.

The PD cycler 802, as shown in FIG. 7, is seated on a cart 804. The PD cycler 802 includes a housing 806, a door 808, and a cassette interface that contacts a disposable PD cassette of the disposable set when the cassette is disposed within a cassette compartment formed between the cassette interface and the closed door 808. The disposable set further includes dialysate bags 822 that are suspended from fingers on the sides of cart 804. The dialysate bags 822 are connected to the cassette via dialysate bag lines 826. The dialysate bag lines 826 can be used to pass dialysate from dialysate bags 822 to the cassette during a fill phase of an APD treatment cycle.

A patient line 830 and a spent dialysate line 832 are connected to the cassette. The patient line 830 can be connected to a patient's abdomen via a catheter and can be used to pass dialysate back and forth between the cassette and the patient's peritoneal cavity during treatment. The spent dialysate line 832 can be fluidly connected to a drain or a drain bag and can be used to pass spent dialysate from the cassette to the drain or drain bag during treatment.

Still referring to FIG. 7, the PD system 800 includes a spent dialysate testing system 850 for testing spent dialysate flowing along the spent dialysate line 832 during treatment. The spent dialysate testing system 850 includes a cuvette 852 that is fluidly coupled to the spent dialysate line 832 using a fluid line 866. The spent dialysate testing system 850 includes an emitter 854 and a spectroscopy sensor 856 positioned on the housing 806 of the PD cycler 802. During treatment, the cuvette 852 is attached to the housing 806 between the emitter 854 and the spectroscopy sensor 856.

As can be seen in FIG. 7, the PD cycler 802 includes a door 880 coupled to the housing 806 of the PD cycler 802 proximate the spent dialysate testing system 850. The door 880 is configured to cover the spent dialysate testing system 850 during testing of spent dialysate in the cuvette 852. For example, the door 880 can be placed in an open position (as depicted in FIG. 7) to allow an operator to attach a cuvette 852 to the housing 806 of the PD cycler 802, and, once the cuvette 852 is attached to the housing 806, the door 880 can be closed to cover the cuvette 852, emitter 854, and spectroscopy sensor 856 for testing spent dialysate within the cuvette 852.

Similar to the cuvettes 302, 306, 304, cuvette 852 contains a PiColorLock™ Phosphate Detection reagent that is configured to react with the sample of spent dialysate that flows from the spent dialysate line 832 into the cuvette 852. The reagent solution contained in the cuvette 852 reacts with the spent dialysate to generate chemical compounds that are indicative of a level of phosphate within the spent dialysate. The chemical compounds generated by reacting the spent dialysate with the reagent within the cuvette have a chromophore that is detectable using low-cost spectroscopy methods.

The cuvette 852 includes a vent 858 configured to release gas by-products generated by the reaction of the reagent and the spent dialysate within the cuvette 852. The cuvette 852 also includes a frangible connector 860, which is positioned within a mechanical frangible breaking mechanism 862 on the housing 806 of the PD cycler 802. Similar to the mechanical frangible breaking mechanisms 326, 328, 330, the frangible breaking mechanism 862 crushes or otherwise breaks the frangible connector 860 to fluidly connect the cuvette 852 to the fluid line 866 and the spent dialysate line 832.

Similar to the emitters 342, 344, 346 of FIG. 2, the emitter 854 includes one or more light emitting diodes (LEDs) that are configured to generate and emit electromagnetic radiation. For example, during testing of the spent dialysate within the cuvette 852, the emitter 854 emits a beam of light along the length of the cuvette 852.

As with the spectroscopy sensors 352, 354, 356 of FIG. 2, the spectroscopy sensor 856 is configured to measure the electromagnetic spectrum passing through the fluid contained within the cuvette 852. The spectroscopy sensor 856 is communicably coupled to the controller 840 of the PD cycler 802 and is configured to transmit signals indicating the detected electromagnetic spectrum to the controller 840. The controller 840 determines a level of one or more waste products present in the spent dialysate in the cuvette 852 based on the signals received from the spectroscopy sensor 856.

A process of testing for the presence of phosphate within spent dialysate using the spent dialysate testing system 850 will now be described with reference to FIG. 7. At the beginning of the drain phase of a PD treatment, a valve 864 along the fluid line 866 is closed and a valve 868 along the spent dialysate line 832 is open. As a result, spent dialysate is prevented from flowing into the cuvette 852 at the beginning of treatment and is instead directed to the drain or drain bags via spent dialysate line 832. As treatment proceeds, spent dialysate flows from the patient's peritoneal cavity, through the PD cassette, and along the spent dialysate line 832 towards a drain or drain bag.

After a predetermined amount of time has elapsed from the start of the drain phase of the PD treatment, the controller 140 controls the valve 868 positioned along the spent dialysate line 832 downstream of the cuvette 852 to close and the valve 864 along the fluid line 866 to open. The controller 140 simultaneously causes the frangible breaking mechanism 862 to break the frangible connector 860 in order to fluidly couple cuvette 852 to the spent dialysate line 832 via the fluid line 866. In some implementations, the controller 140 causes the valve 868 to close, the valve 864 to open, and the frangible breaking mechanism 862 to break the frangible connector 860 about 2 minutes to about 5 minutes after the start of the drain phase of the PD treatment.

Once the valve 868 is closed, the valve 864 is open, and the frangible connector 860 is broken, spent dialysate flowing along the spent dialysate line 832 is directed into the cuvette 852. After a sufficient volume of spent dialysate is provided to the cuvette 852, the controller 840 of the PD cycler 802 causes the valve 864 along the fluid line 866 to close and the valve 868 along the spent dialysate line 832 to open, trapping the spent dialysate within the cuvette 852 and allowing the spent dialysate flowing along the spent dialysate line 832 to be directed towards a drain or drain bag. In some implementations, the controller 840 causes the valve 864 to close and causes the valve 864 to open about 2 second to about 8 seconds after initially opening the valve 864 and closing the valve 864. In some implementations, the amount of time the valve 864 is open is dependent on the outflow rate of spent dialysate flowing along spent dialysate line 832 and the volume of spent dialysate required to perform the testing.

Once spent dialysate has been provided to the cuvette 852 and the valve 864 is closed, the spent dialysate contained within the cuvette 852 mixes and reacts with the reagent contained within the cuvette 852. As the spent dialysate reacts with the reagent in the cuvette 852, any gases resulting from the reaction are released from the cuvette 852 through the vent 858. The spent dialysate reacts with the reagent in the cuvette 852 to form a compound that has a chromophore detectable using spectroscopy. Once the reaction between the spent dialysate and the reagent in the cuvette 852 is complete, the controller 840 controls the emitter 854 to transmit UV-vis radiation through the solution contained within the cuvette 852 towards the spectroscopy sensor 856. As the UV-vis radiation is absorbed and reflected by the solution contained within the cuvette 852, the resulting electromagnetic spectrum is detected by the spectroscopy sensor 856.

The electromagnetic spectrum detected by the spectroscopy sensor 856 is transmitted to the controller 840 of the PD cycler 802, and the controller 840 determines a level of phosphate present in the spent dialysate at the time of testing based on the electromagnetic spectrum detected by the spectroscopy sensor 856. In some implementations, the controller 840 causes a screen 818 of the PD cycler 802 to display the detected phosphate level in real time.

In some implementations, if the level of phosphate detected by the spectroscopy sensors 856 is above 6.5 mg/dL, the controller 840 causes the screen 818 of the PD cycler 802 to display a warning in real time indicating a high phosphate level. In some implementations, if the detected level of phosphate is above a threshold level (e.g., 6.5 mg/dL), the controller 840 causes the PD cycler 802 to alert the user to seek immediate medical intervention. In some implementations, if the detected level of phosphate is above 6.5 mg/dL, the controller 840 causes the PD cycler 802 to provide a recommendation to change the frequency of treatment (e.g., to increase treatment frequency). In some implementations, if the detected level of phosphate is above a predetermined threshold, the controller 840 causes the PD cycler 802 to transmit an alert to computing devices of one or more clinicians indicating the detected phosphate level. In some implementations, one or more treatment parameters of the dialysate treatment are adjusted in response to detecting that the detected phosphate level in the spent dialysate exceeds a threshold level.

Dialysis treatment continues while the spent dialysate is tested within the cuvette 852. After treatment is completed, the cuvette 852 is detached from the PD cycler 802 and discarded. A new, unused cuvette can be coupled to the PD cycler 802 in preparation for the next treatment to be performed using the PD cycler 802.

While FIG. 7 depicts the cuvette 852 and spent dialysate testing system 850 as being coupled to the housing 806 of the PD cycler 802, in some implementations, the spent dialysate testing system is contained within a housing that is separate from the housing 806 of the PD cycler 802 and fluidly coupled to the spent dialysate line 832, and the cuvette 852 is positioned within the separate housing of the spent dialysate testing system.

Figure 8:
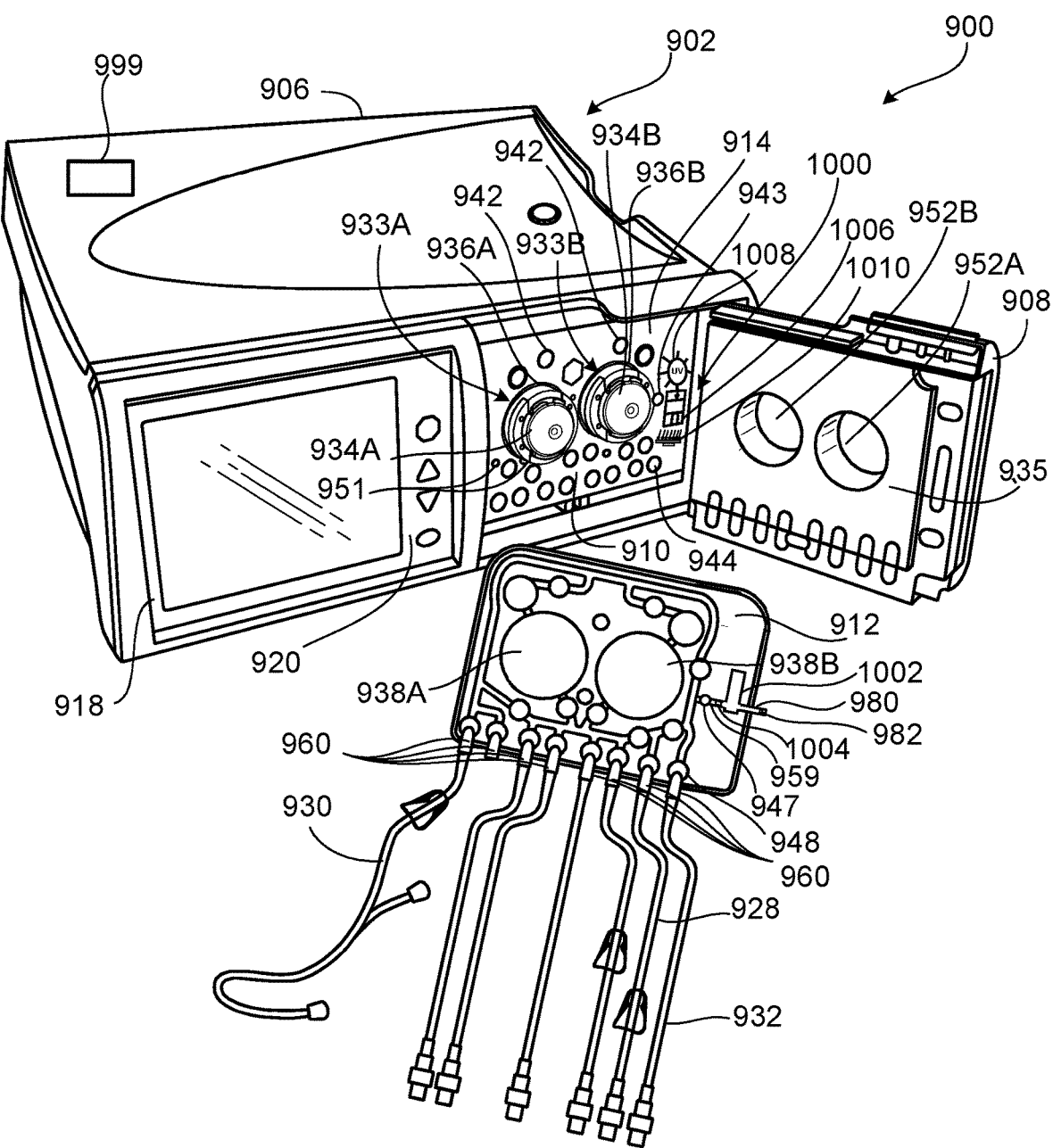
FIG. 8 is a perspective view of another PD treatment system that includes a spent dialysate testing system.

In addition, while FIG. 7 depicts the cuvette 852 of the spent dialysate testing system 850 as being coupled to the outside of the housing 806 of the PD cycler 802, in some implementations, a fluid receptacle for testing spent dialysate is incorporated into the PD cassette. FIG. 8 depicts an example PD system 900 with an alternate spent dialysate testing system 1000 for testing spent dialysate. The PD system 900 includes a PD cycler and a cassette 912 configured to be attached to the PD cycler 902.

Figure 9:
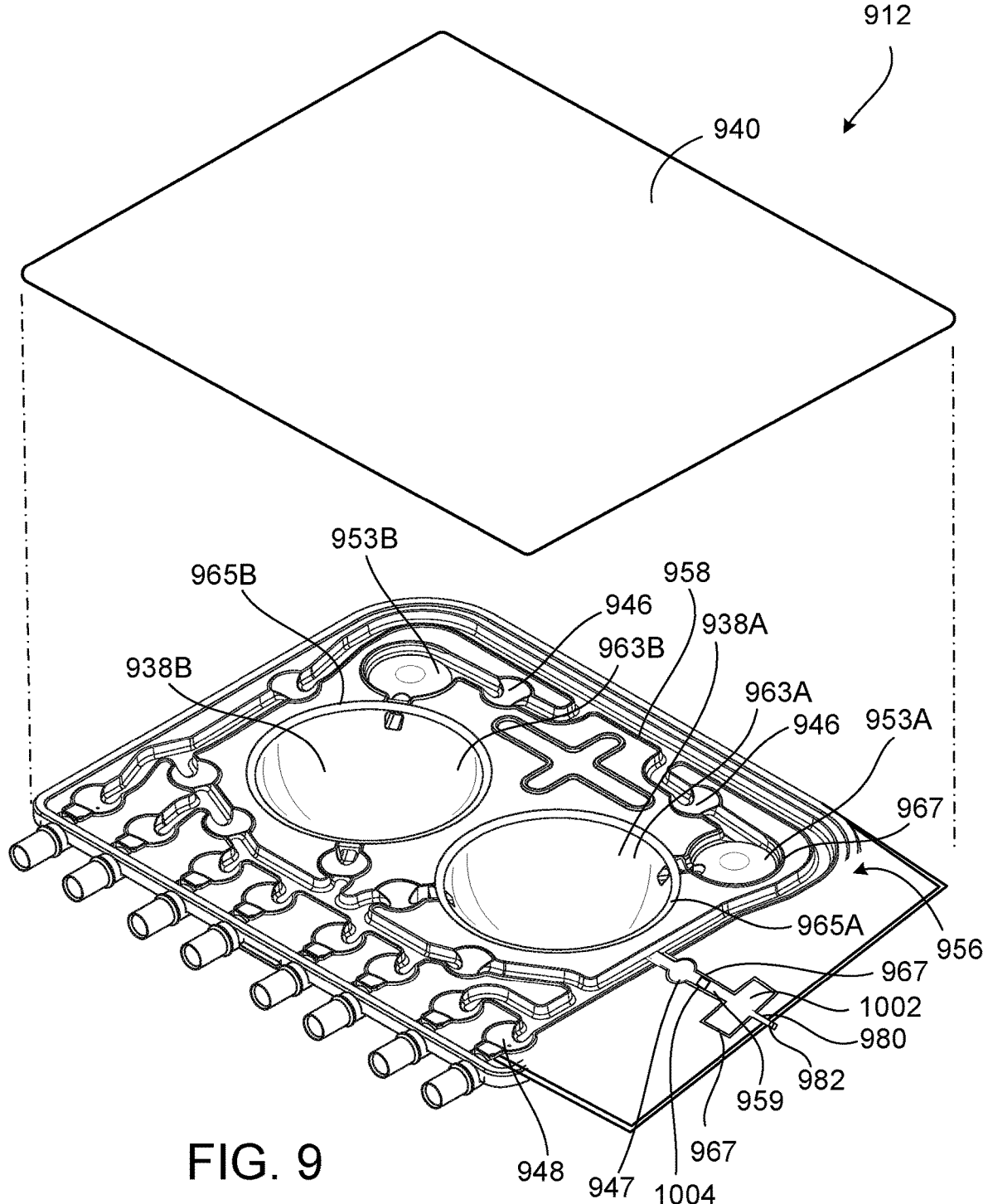
FIG. 9 is an exploded, perspective view of the PD cassette of the PD treatment system of FIG. 8.

FIG. 9 depicts PD cassette 912 of the PD system 900. As shown in FIG. 9, the cassette 912 includes the tray-like rigid base 956 and a flexible membrane 940, which is attached to the periphery of the base 956 when cassette 912 is fully assembled. The base 956 includes recessed regions 963A, 963B that partially define pump chambers 938A, 938B of the cassette 912. Raised ridges 965A, 965B extend from a planar surface of the base 956 around each of the recessed regions 963A, 963B and extend towards and into contact with the inner surface of the flexible membrane 940 when the cassette 912 is compressed between the door 908 and the cassette interface 910 of the PD cycler 902. In addition to raised ridges 965A, 965B surrounding the recessed regions 963A, 963B, a series of raised ridges 967 extend from the planar surface of the base 956 towards and into contact with the inner surface of flexible membrane 940 when cassette 912 is compressed between door 908 and the cassette interface 910 of the PD cycler 902.

The recessed regions 963A, 963B of the base 956 cooperate with flexible membrane 940 to form pump chambers 938A, 938B when cassette 912 is compressed between door 908 and the cassette interface 910 of the PD cycler 902, resulting in the flexible membrane 940 being pressed against the raised ridges 965A, 965B of the base 956. In particular, the volumes between the membrane 940 and the hollow projections that form the recessed regions 963A, 963B of the base 956 serve as pump chambers 938A, 938B. The membrane 940, when compressed against the base 956, similarly cooperates with the raised ridges 967 extending from the base 956 to form a series of fluid pathways 958, 959 and to form multiple, depressible dome regions 946, 947, 948 which are widened portions (e.g., substantially circular widened portions) of the fluid pathways 958, 959. The membrane 940, when compressed against the base 956, also cooperates with certain raised ridges 967 to form pressure sensor chambers 953A, 953B.

During treatment, liquid, such as dialysate, flows to and from the pump chambers 938A, 938B through the fluid pathways 958, 959 and dome regions 946, 947, 948. At each depressible dome region 946, 947, 948, the membrane 940 can be deflected to contact the planar surface of the base 956 from which the raised ridges 967 extend. Such contact can substantially impede (e.g., prevent) the flow of dialysate along the region of the fluid pathway 958 associated with that dome region 946, 947, 948. Thus, the flow of dialysate through the cassette 912 can be controlled through the selective depression of the depressible dome regions 946, 947, 948 by selectively inflating mating inflatable members on the cassette interface 910 of the PD cycler 902.

As noted above, the membrane 940 is attached (e.g., adhesively and/or thermally bonded) to the periphery of the base 956. The portion of the membrane 940 overlying the central portion of the base 956 is not necessarily attached to base 956. Rather, this portion of the membrane 940 may sit loosely atop the raised ridges 965A, 965B, 967 extending from the planar surface of the base 956. The thickness and material(s) of the membrane 940 are selected so that the membrane 940 has sufficient flexibility to flex toward the base 956 in response to the force applied to the membrane 940 by piston heads and inflatable members of the PD cycler 902. In certain implementations, the membrane 940 is about 0.100 micron to about 0.150 micron in thickness. However, various other thicknesses may be sufficient depending on the type of material used to form the membrane 940.

Any of various different medical grade materials that permit the membrane 940 to deflect in response to movement of the piston heads and inflation of the inflatable members of the PD cycler 902 without tearing can be used to form the membrane 940. In some implementations, the membrane 940 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane 940 can alternatively include more or fewer layers and/or can be formed of different materials.

As shown in FIG. 8, fluid line connectors 960 are positioned along the bottom edge of cassette 912. The fluid pathways 958 in the cassette 912 lead from the pumping chambers 938A, 938B to the various connectors 960. The connectors 960 are configured to receive fittings on the ends of the dialysate bag lines 926, a heater bag line 928, the patient line 930, and the spent dialysate line 932. One end of the fitting can be inserted into and bonded to its respective line and the other end can be inserted into and bonded to its associated connector 960. By permitting the dialysate bag lines 926, the heater bag line 928, the patient line 930, and the spent dialysate line 932 to be connected to the cassette 912, as shown in FIG. 8, the connectors 960 allow dialysate to be pumped into and out of the cassette 912 during use.

As can be seen in FIG. 9, the raised ridges 967 define a fluid path 959 into a fluid receptacle 1002 configured to receive spent dialysate flowing through the cassette 912. Similar to the cuvettes 302, 304, 306, the fluid receptacle 1002 contains a PiColorLock™ Phosphate Detection reagent that is configured to react with the sample of spent dialysate that flows through the fluid paths 958, 959 into the fluid receptacle 1002. The reagent contained within the fluid receptacle 1002 reacts with the spent dialysate to generate chemical compounds that have a chromophore detectable using spectroscopy that is indicative of a level of phosphate within the spent dialysate.

The raised ridges 967 define also a dome region 947 along the fluid path 959 that can be depressed by inflating a mating inflatable member on the cassette interface 910 of the PD cycler 902 in order to control flow through the fluid path 959 to the fluid receptacle 1002. In addition, the cassette 912 includes a frangible connector 1004, which is configured to prevent flow of the reagent out of the fluid receptacle 1002 as well as prevent flow of spent dialysate through the fluid path 959 into the fluid receptacle 1002 until broken by a breaking mechanism 1006 of the PD cycler 902. As will be described in further detail herein, when cassette 912 is positioned within the cassette interface 910 of the PD cycler 902, the fluid receptacle 1002 is aligned along its length between an emitter 1008 and a spectroscopy sensor 1010 of the spent dialysate testing system 1000 to allow for spectroscopic analysis of the spent dialysate provided to the fluid receptacle 1002.

As shown in FIG. 8, PD cycler 902 includes pistons 933A, 933B with piston heads 934A, 934B attached to piston shafts that can be axially moved within piston access ports 936A, 936B formed in the cassette interface 910. The pistons 933A, 933B, the piston heads 934A, 934B, and the corresponding piston shafts are sometimes referred to herein as pumps. Piston access ports 936A, 936B form annular passages that surround the piston heads 934A, 934B and are in fluid communication with portions of the cassette membrane 940 overlying the pump chambers 938A, 938B when the cassette 912 is disposed in the cassette compartment 914 of the PD cycler 902. As a result, vacuum pressure applied to the annular passages that surround the piston heads 934A, 934B can be used to draw the membrane 940 of cassette 912 against the piston heads 934A, 934B.

The pistons 933A, 933B are coupled to motors that can be operated to move the piston heads 934A, 934B axially inward and outward within the piston access ports 936A, 936B. When the cassette 912 is positioned within the cassette compartment 914 with the door 908 closed, the piston heads 934A, 934B of the PD cycler 902 align with pump chambers 938A, 938B of the cassette 912. As a result, the piston heads 934A, 934B can be moved in the direction of the cassette 912 to force the membrane 940 of the cassette 912 toward the rigid base 956, causing the volume defined by the pump chambers 938A, 938B to decrease and forcing dialysate out of the pump chambers 938A, 938B. The piston heads 934A, 934B can also be retracted away from the base 956 of cassette 912. Portions of the cassette membrane 940 overlying the pump chambers 938A, 938B are drawn toward the piston heads 934A, 934B with vacuum force as the pistons heads 934A, 934B are retracted. In particular, the annular passages surrounding the piston heads 934A, 934B can be used to apply a vacuum force to those portions of the membrane 940 overlying the pump chambers 938A, 938B. The piston access ports 936A, 936B are connected to a vacuum source (e.g., an air pump or vacuum reservoir) to allow the vacuum pressure to be applied to the membrane 940 of the cassette 912 via the annular passages. As a result, the volume defined by the pump chambers 938A, 938B increases and dialysate is drawn into the pump chambers 938A, 938B as the piston heads 934A, 934B retract together with respective portions of the cassette membrane 940.

As shown in FIG. 8, the PD cycler 902 also includes multiple inflatable members 942, 943, 944 positioned within inflatable member access ports in the cassette interface 910. The inflatable members 942, 943, 944 align with the depressible dome regions 946, 947, 948 of the cassette 912 when the cassette 912 is positioned within the cassette compartment 914. The inflatable members 942, 943 are connected to fluid lines that act as conduits for applying positive pressure and/or vacuum pressure to inflatable members 942, 943, 94 such that the inflatable members 942, 943, 944 can be inflated and deflated during use. While not all of the inflatable members 942, 943,944 are labeled in FIG. 8, it should be understood that the PD cycler 902 includes an inflatable member associated with each of the depressible dome regions 946, 947 of the cassette 912 (shown in FIG. 9). The inflatable members 942, 943, 944 act as valves to direct dialysate through the cassette 912 in a desired manner during use. In particular, the inflatable members 942, 943, 944 bulge outward beyond the surface of the cassette interface 910 and into contact with the depressible dome regions 946, 947,948 of the cassette 912 when inflated, and retract into the inflatable member access ports and out of contact with the cassette 912 when deflated. By inflating certain inflatable members 942, 943, 944 to depress their associated dome regions 946, 947,948 on the cassette 912, certain fluid flow paths within the cassette 912 can be blocked off. Thus, dialysate can be pumped through the cassette 912 by actuating the piston heads 934A, 934B, and can be guided along desired flow paths within the cassette 912 by selectively inflating and deflating the inflatable members 942, 943, 944.

Still referring to FIG. 8, the cassette interface 910 also includes vacuum ports 951 that are connected to vacuum lines positioned within the housing 906 of the PD cycler 902. The vacuum ports 951 allow vacuum pressure to be applied to the cassette membrane 940 when the cassette 912 is positioned adjacent to the cassette interface 910. Applying vacuum pressure to the membrane 940 through the vacuum ports 951 draws the membrane 940 toward the cassette interface 910, thereby forming a seal between the cassette interface 910 and the membrane 940.

The door 908, as shown in FIG. 8, defines recesses 952A, 952B that substantially align with the piston heads 934A, 934B when the door 908 is in the closed position. When the cassette 912 is positioned within the cassette compartment 914, hollow projections that form the recessed regions 963A, 963B in the base 956 of cassette 912 and cooperate with the membrane 940 to form the pump chambers 938A, 938B fit within the recesses 952A, 952B in door 908. An inflatable pad 935 in door 908 can be inflated during use to compress the cassette 912 between the door 908 and the cassette interface 910. With the inflatable pad 935 inflated, portions of the door 908 forming the recesses 952A, 952B support the hollow projections of the base 956 of the cassette 912 and the planar surface of door 908 supports the other regions of the base 956 of cassette 912. The door 908 can counteract the forces applied by the piston heads 934A, 934B and the inflatable members 942 and thus allows piston heads 934A, 934B to depress portions of the cassette membrane 940 overlying the pump chambers 938A, 938B and similarly allows the inflatable members 942, 943 to actuate depressible dome regions 946 on the cassette 912.

A method of operating the PD cycler 902 will now be described with reference to FIGS. 8 and 9. Before treatment, the door 908 of the PD cycler 902 is opened to expose the cassette interface 910, and the cassette 912 is positioned with its membrane 940 adjacent to the cassette interface 910. The cassette 912 is positioned such that the pump chambers 938A, 938B are aligned with the piston heads 934A, 934B, and the depressible dome regions 946, 947, 948 of the cassette 912 are aligned with the inflatable members 942, 943, 944, respectively. In addition, the cassette 912 is positioned such that fluid receptacle 1002 of the cassette 912 is positioned between the emitter 1008 and the spectroscopy sensor 1010, and the frangible connector 1004 is positioned within the frangible breaking mechanism 1006 in the cassette compartment 914.

After loading the cassette 912 into the cassette compartment 914 of the PD cycler 902, positive pressure is supplied to the inflatable pad 935. The positive pressure inflates the inflatable pad 935 to secure the cassette 912 within the cassette compartment 914 in a manner such that the membrane 940 of the cassette 912 is pressed firmly against the cassette interface 910 of the PD cycler 902. In addition, vacuum pressure is supplied to the vacuum ports 951 to form a seal between the membrane 940 and the cassette interface 910. Vacuum pressure is also applied to the annular passages surrounding the piston heads 934A, 934B. The vacuum pressure is supplied from an air pump and/or a vacuum reservoir.

With the cassette 912 loaded into the cassette compartment 914, the membrane 940 of the cassette 912 covers the annular passages surrounding the piston heads 934A, 934B. As a result, when the piston heads 934A, 934B are retracted away from the cassette 912 during use, the vacuum pressure applied to the membrane 940 via the annular passages causes the portions of the membrane 940 overlying the piston heads 934A, 934B to be drawn toward the cassette interface 910 in unison with the retracting piston heads 934A, 934B. As a result, the volume defined by the pump chambers 938A, 938B increases, and, depending on the state of the inflatable members 942, dialysate can be drawn into the pump chambers 938A, 938B as the piston heads 934A, 934B retract together with respective portions of the membrane 940. Similarly, depending on the state of the various inflatable members 942, as the piston heads 934A, 934B are advanced, the volume of the pump chambers 938A, 938B decreases, forcing dialysate from the pump chambers 938A, 938B into the fluid paths 958 of the cassette 912.

As the pistons 932A, 932B of the PD cycler 902 reciprocate, each of the inflatable members 942, 943, 944 is either inflated or deflated to control the flow of dialysate through the cassette 912. To inflate the inflatable members 942, 943, 944 positive pressure is applied from an air pump to an inflatable member valve manifold. The valves of the inflatable member valve manifold are operated in a manner to deliver the positive pressure only to those inflatable members 942, 943, 944 that are to be or remain inflated. To deflate the inflatable members 942, 943, 944, vacuum pressure is supplied from an air pump and/or a vacuum reservoir to the inflatable member valve manifold. The valves of the inflatable member valve manifold are operated in a manner to deliver the vacuum pressure only to those inflatable members 942, 943, 944 that are to be or remain deflated.

During the drain phase of the PD treatment, the piston heads 934A, 934B are advanced and retracted to flow spent dialysate from the patient's peritoneal cavity through the patient line 930, through the fluid paths 958 of cassette 912, and out of the cassette 912 through the spent dialysate line 932 to a drain or drain bag. At the beginning of the drain phase of the PD treatment, the inflatable member 943 is inflated to depress the dome region 947 along the fluid path 959 in order to prevent spent dialysate from flowing through the fluid path 959 to the fluid receptacle 1002.

After a predetermined amount of time has elapsed from the start of the drain phase of the PD treatment, a controller 999 of the PD cycler 902 controls an air pump and/or a vacuum source to apply vacuum pressure to the inflatable member 943, which increases the volume within the dome region 947 to allow spent dialysate to flow through the dome region 947 into the fluid path 959. The controller 999 simultaneously controls an air pump to apply positive pressure to the inflatable member 944 to depress the dome region 948, which prevents flow out of the cassette 912 along the spent dialysate line 932. The controller 999 also simultaneously controls the frangible breaking mechanism 1006 to break the frangible connector 1004 in order to fluidly couple the fluid receptacle 1002 with the fluid path 958 via the fluid path 959. In some implementations, the controller 999 causes the inflatable member 943 to deflate, the inflatable member 944 to inflate, and the frangible breaking mechanism 1006 to break the frangible connector 1004 about 2 minutes to about 5 minutes after the start of the drain phase of the PD treatment.

Once inflatable member 943 is deflated, the inflatable member 944 is inflated, and the frangible connector 1004 is broken, spent dialysate flowing along fluid path 958 is directed into the fluid receptacle 1002. After a sufficient volume of spent dialysate is provided to the fluid receptacle 1002, the controller 999 of the PD cycler 902 causes the inflatable member 943 to inflate and causes the inflatable member 944 to deflate, trapping the spent dialysate within the fluid receptacle 1002 and allowing spent dialysate flowing along the fluid path 958 to flow through the spent dialysate line 932 towards a drain or a drain bag. In some implementations, the controller 999 causes the inflatable member 943 to inflate and causes the inflatable member 944 to deflate about 1 second to about 3 seconds after initially deflating the inflatable member 943 and inflating the inflatable member 944. In some implementations, the amount of time the inflatable member 943 is deflated and the inflatable member 944 is inflated is dependent on the flow rate of spent dialysate flowing through the cassette 912 and the volume of spent dialysate required to perform the testing.

Once spent dialysate has been provided to the fluid receptacle 1002 and the inflatable member 943 is inflated, the spent dialysate contained within the fluid receptacle 1002 mixes and interacts with a PiColorLock™ Phosphate Detection reagent contained within the fluid receptacle 1002. The spent dialysate reacts with the reagent in the fluid receptacle 1002 to form a compound that has a chromophore detectable using spectroscopy. As can be seen in FIGS. 8 and 9, the cassette defines a vent tube 980 that is configured to release gas by-products generated by reacting the reagent with spent dialysate within the receptacle 1002. A hydrophobic filter 982 is positioned along the vent line 980 to prevent the fluid contained within the fluid receptacle from escaping the cassette 912. In some implementations, the length of the vent tube 980 is about 15 cm to about 20 cm.

Once the reaction between the spent dialysate and the reagent in the fluid receptacle 1002 is complete, the controller 999 controls emitter 1008 to transmit UV-vis radiation at a wavelength of about 625 nm through the solution contained within fluid receptacle 1002 towards spectroscopy sensor 1010. As the UV-vis radiation is absorbed and reflected by the solution contained within the fluid receptacle 1002, the resulting electromagnetic spectrum is detected by spectroscopy sensor 1010.

The electromagnetic spectrum detected by the spectroscopy sensor 1010 is transmitted to the controller 999 of the PD cycler 902, and the controller 999 determines a level of phosphate present in the spent dialysate at the time of testing based on the electromagnetic spectrum detected by the spectroscopy sensor 1010. In some implementations, the controller 999 causes a screen 918 of the PD cycler 902 to display the detected phosphate level in real time.

In some implementations, if the level of phosphate detected by the spectroscopy sensors 1010 is above 6.5 mg/dL, the controller 999 causes the screen 918 of the PD cycler 902 to display a warning in real time indicating a high phosphate level. In some implementations, if the detected level of phosphate is above a threshold level (e.g., 6.5 mg/dL), the controller 999 causes the PD cycler 902 to alert the user to seek immediate medical intervention. In some implementations, if the detected level of phosphate is above 6.5 mg/dL, the controller 999 causes the PD cycler 902 to provide a recommendation to change the frequency of treatment (e.g., to increase treatment frequency). In some implementations, if the detected level of phosphate is above a predetermined threshold, the controller 999 causes the PD cycler 902 to transmit an alert to computing devices of one or more clinicians indicating the detected phosphate level. In some implementations, one or more treatment parameters of the dialysate treatment are adjusted in response to detecting that the detected phosphate level in the spent dialysate exceeds a threshold level.

Dialysis treatment continues while the spent dialysate is tested within fluid receptacle 1002. After treatment is completed, the cassette 912 is detached from PD cycler 902 and discarded. In addition, a new, unused cassette can be coupled to the PD cycler 902 in preparation for the next treatment to be performed using the PD cycler 902.

While the cuvettes 302, 304, 306, 702, 704, 852 and fluid receptacle 1002 have been described as containing PiColorLock™ Phosphate Detection reagent to react with spent dialysate in order to detect a concentration of phosphate in the spent dialysate, in some implementations, cuvettes 302, 304, 306, 702, 704, 852 and fluid receptacle 1002 each contain Phosphate HR tablets available from Tintometer Inc. to detect the concentration of phosphate in the spent dialysate. For example, the Phosphate HR tablets contained within the cuvettes 302, 304, 306, 702, 704, 852 and fluid receptacle 1002 react with spent dialysate provided to the respective cuvettes 302, 304, 306, 702, 704, 852 and fluid receptacle 1002 to generate a compound that has a chromophore that is detectable using electromagnetic spectroscopy. Once spent dialysate has been provided to the respective cuvette 302, 304, 306, 702, 704, 852 or fluid receptacle 1002 and the spent dialysate has reacted with the Phosphate HR tablet contained within the respective cuvette 302, 304, 306, 702, 704, 852 or fluid receptacle 1002, spectroscopy can be performed on the reacted solution, as described above, to detect the concentration of phosphate within the spent dialysate.

In some implementations, the concentration of phosphate within the spent dialysate is detected by reacting the spent dialysate with a molybdenum reagent solution. For example, in some implementations, each of the cuvettes 302, 304, 306, 702, 704, 852 and fluid receptacle 1002 contain a reagent solution of nitric acid and ammonium molybdate, and the spent dialysate provided to the cuvettes 302, 304, 306, 702, 704, 852 and fluid receptacle 1002 reacts with the reagent solution to form ammonium phosphomolybdate, which is yellow in color and can be detected using UV-vis spectroscopy, as described above. In some implementations, the reaction between the spent dialysate and the nitric acid and ammonium molybdate solution is facilitated by heating the solution in the respective cuvette 302, 304, 306, 702, 704, 852 or fluid receptacle 1002. In some implementations, the nitric acid and ammonium molybdate are each initially contained in separate receptacles that are separated from one another by frangibles, and the controller 140, 840, 999 of the respective dialysis machine 102, 802, 902 operates frangible breaking mechanisms shortly before or at the time of testing in order to fluidly couple the receptacles and form the reagent solution. The reagent solution can then be provided to the respective cuvette 302, 304, 306, 702, 704, 852 or fluid receptacle 1002 for reacting with the reagent solution with the spent dialysate (e.g., by breaking a frangible to fluidly couple the respective cuvette 302, 304, 306, 702, 704, 852 or fluid receptacle 1002 with the receptacles containing the reagent solution). UV-vis spectroscopy can then be performed on the reacted solution, as described above, to detect the concentration of phosphate within the spent dialysate. This testing method can also be used to detect a concentration of arsenic within the spent dialysate.

In some implementations, each of the cuvettes 302, 304, 306, 702, 704, 852 and fluid receptacle 1002 contain a reagent solution containing sulfuric acid, potassium antimonyl tartrate, ammonium molybdate, and ascorbic acid, which reacts with spent dialysate to form heteropolymolybdate, which has a pale yellow chromophore that is detectable using UV-vis spectroscopy. In some implementations, the sulfuric acid, potassium antimonyl tartrate, ammonium molybdate, and ascorbic acid are each initially contained in separate receptacles that are separated from one another by frangibles, and the controller 140, 840, 999 of the respective dialysis machine 102, 802, 902 operates frangible breaking mechanisms and provide DI water to the receptacles shortly before or at the time of testing in order to fluidly couple the receptacles and form the reagent solution. The reagent solution can then be provided to the respective cuvette 302, 304, 306, 702, 704, 852 or fluid receptacle 1002 for reacting with the reagent solution with the spent dialysate (e.g., by breaking a frangible to fluidly couple the respective cuvette 302, 304, 306, 702, 704, 852 or fluid receptacle 1002 with the receptacles containing the reagent solution). UV-vis spectroscopy can then be performed on the reacted solution, as described above, to detect the concentration of phosphate within the spent dialysate.

In some implementations, the concentration of phosphate within the spent dialysate is detected by reacting the spent dialysate with a solution of an ammonium heptamolybdate reagent and a stannous chloride reagent. For example, the respective dialysis machine 102, 802 can include a receptacle that contains ammonium heptamolybdate reagent, which, prior to testing, is shaken (e.g., using one or more of the mixing methods described above). After the ammonium heptamolybdate reagent has been vigorously shaken, the controller 140, 840, 999 of the respective dialysis machine 102, 802, 902 can operate a frangible breaking mechanism to fluidly couple the receptacle containing the shaken ammonium heptamolybdate reagent with another receptacle containing concentrated stannous chloride reagent and distilled water (e.g., that has been provided by the dialysis machine 102, 802, 902 to the receptacle containing concentrated stannous chloride reagent) to form a final reagent solution. The controller 140, 840, 999 can then control the respective dialysis machine 102, 802, 902 to provide the final reagent solution to a respective cuvette 302, 304, 306, 702, 704, 852 or fluid receptacle 1002 (e.g., by operating a frangible breaking mechanism to break a frangible that separates the respective cuvette 302, 304, 306, 702, 704, 852 or fluid receptacle 1002 from the receptacle containing the final reagent solution). The spent dialysate contained within the respective cuvette 302, 304, 306, 702, 704, 852 or fluid receptacle 1002 reacts with the final reagent solution to form a molybdenum compound that has a blue chromophore detectable using UV-vis spectroscopy. UV-vis spectroscopy can then be performed on the reacted solution, as described above, to detect the concentration of phosphate within the spent dialysate.

While the spent dialysate testing systems 300, 400, 500, 600, 700, 850, 1000 have been described as being used to determine a level of phosphate within the spent dialysate, the spent dialysate testing systems 300, 400, 500, 600, 700, 850, 1000 can be used to detect other compounds contained within spent dialysate. For example, the cuvettes 302, 304, 306, 702, 704, 852 and fluid receptacle 1002 can contain an Alizarin reagent solution containing Alizarin Red S and the spent dialysate testing systems 300, 400, 500, 600, 700, 850, 1000 can each be configured to detect a level of calcium in the spent dialysate. The spent dialysate testing systems 300, 400, 500, 600, 700, 850, 1000 can determine a level of calcium in the spent dialysate by reacting samples of the spent dialysate with the Alizarin reagent solution contained in the respective cuvettes 302, 304, 306, 702, 704, 852 or fluid receptacle 1002, transmitting electromagnetic radiation (e.g., UV light) at a wavelength of above 440 nm to about 460 nm through the reacted solution using the respective emitter 342, 344, 346, 442, 444, 446, 742, 854, 1008, detecting the resulting electromagnetic spectrum using a respective spectroscopy sensor 352, 354, 356, 452, 454, 456, 752, 856, 1010 and analyzing the detected electromagnetic spectrum to determine a level of calcium in the spent dialysate. The Alizarin reagent solution contained in the cuvettes 302, 304, 306 for detecting calcium contains an acid with a pH sufficient to lower the pH of the reacted sample to below 5.2. By lowering the pH of the reacted dialysate sample to below 5.2, the Alizarin Red S of the reagent solution will stain calcium within the spent dialysate and produce a compound that has a chromophore detectable using spectroscopy. The chromophore of the compound produced by reacting the spent dialysate with the Alizarin reagent solution is detectable with light wavelengths of 440 nm to 460 nm.

In some implementations, the cuvettes 302, 304, 306, 702, 704, 852 and fluid receptacle 1002 contain a picric acid reagent solution and the respective spent dialysate testing systems 300, 400, 500, 600, 700, 850, 1000 are each configured to detect a level of creatinine in the spent dialysate. The spent dialysate testing systems 300, 400, 500, 600, 700, 850, 1000 determine a level of creatinine in the spent dialysate by reacting samples of the spent dialysate with the picric acid reagent solution contained in the respective cuvettes 302, 304, 306, 702, 704, 852 and fluid receptacle 1002, transmitting electromagnetic radiation (e.g., UV light) at a wavelength of about 530 nm through the reacted solution using the respective emitter 342, 344, 346, 442, 444, 446, 742, 854, 1008, detecting the resulting electromagnetic spectrum using a respective spectroscopy sensor 352, 354, 356, 452, 454, 456, 752, 856, 1010, and analyzing the detected electromagnetic spectrum to determine a level of creatinine in the spent dialysate. In some implementations, the compound produced by reacting the spent dialysate with the picric acid reagent has a chromophore that is a violet color and has a maximum absorbance using light wavelengths of about 530 nm. The picric acid reagent solution contained in the cuvettes 302, 304, 306, 702, 704, 852 and fluid receptacle 1002 for detecting creatinine is an alkaline solution.

In some implementations, the cuvettes 302, 304, 306, 702, 704, 852 and fluid receptacle 1002 each contain one or more reagents that generate a series of coupled enzymatic reactions that can be used to generate a compound having a chromophore that can be detected using spectroscopy to detect a level of creatinine in the spent dialysate. For example, the cuvettes 302, 304, 306, 702, 704, 852 and fluid receptacle 1002 can each contain reagent that results in creatininase enzymatic conversion of creatinine in the spent dialysate into creatine, which is then converted to sarcosine by creatine amidinohydrolase, followed by oxidation of sarcosine by sarcosine oxidase (SOD) producing hydrogen peroxide. The hydrogen peroxide within the respective cuvette 302, 304, 306, 702, 704, 852 or fluid receptacle 1002 further reacts with peroxidase in the reagent solution to generate a compound with a chromophore that can be detected using light wavelengths of about 550 nm. The concentration of the hydrogen peroxide detected in the reacted solution is proportional to the concentration of the creatinine in the spent dialysate.

In some implementations, the cuvettes 302, 304, 306, 702, 704, 852 and fluid receptacle 1002 each contain crown ether 4-aminobenzo-18-crown-6 and crown ether modified gold nanoparticles and the respective spent dialysate testing systems 300, 400, 500, 600, 700, 850, 1000 are each configured to detect a level of potassium in the spent dialysate. The spent dialysate testing systems 300, 400, 500, 600, 700, 850, 1000 determine a level of potassium in the spent dialysate by reacting samples of the spent dialysate with the crown ether 4-aminobenzo-18-crown-6 and crown ether modified gold nanoparticles contained in the cuvettes 302, 304, 306, 702, 704, 852 and fluid receptacle 1002, transmitting electromagnetic radiation (e.g., UV light) through the reacted solution using the respective emitter 342, 344, 346, 442, 444, 446, 742, 854, 1008, detecting the resulting electromagnetic spectrum using a respective spectroscopy sensor 352, 354, 356, 452, 454, 456, 752, 856, 1010 and analyzing the detected electromagnetic spectrum to determine a level of potassium in the spent dialysate.

In some implementations, the cuvettes 302, 304, 306, 702, 704, 852 and fluid receptacle 1002 each contain a mercury ethylenediamine tetraacetic acid (Hg-EDTA) reagent solution and the respective spent dialysate testing systems 300, 400, 500, 600, 700, 850, 1000 are each configured to detect a level of chloride in the spent dialysate. The spent dialysate testing systems 300, 400, 500, 600, 700, 850, 1000 determine a level of chloride in the spent dialysate by reacting samples of the spent dialysate with the Hg-EDTA solution contained in the respective cuvettes 302, 304, 306, 702, 704, 852 and fluid receptacle 1002, transmitting electromagnetic radiation (e.g., UV light) through the reacted solution using the respective emitter 342, 344, 346, 442, 444, 446, 742, 854, 1008, detecting the resulting electromagnetic spectrum using a respective spectroscopy sensor 352, 354, 356, 452, 454, 456, 752, 856, 1010 and analyzing the detected spectrum to determine a level of chloride in the spent dialysate.

In addition, while the cuvettes 302, 304, 306, 702, 704, 852 and fluid receptacle 1002 of the respective spent dialysate testing systems 300, 400, 500, 600, 700, 850, 1000 have been described as each containing a single reagent for detecting a single waste product within the spent dialysate, in some implementations, the cuvettes 302, 304, 306, 702, 704, 852 and fluid receptacle 1002 each contain multiple reagents for simultaneously detecting multiple waste products within the spent dialysate.

Further, while the cuvettes 302, 304, 306 of the spent dialysate testing systems 300, 400, and the cuvettes 702 and 704 of the spent dialysate testing system 700 have each been described as containing the same reagent solution for detecting a single waste product within the spent dialysate during treatment, in some implementations, one or more cuvettes 302, 304, 306, 702, 704 in the respective spent dialysate testing systems 300, 400, 700 can contain different reagent solutions such that the spent dialysate testing systems 300, 400, 700 can be used to detect different waste products within the spent dialysate during treatment.

In some implementations, the spent dialysate testing methods performed by the spent dialysate testing systems 300, 400, 500, 600, 700, 850, 1000 involve multiple intermediate reactions to generate the final reagent solution that is reacted with the spent dialysate. In order to conduct the intermediate reactions to generate the reagent solution, the dialysis machines 102, 802, 902 can include a chain of fluid receptacles (e.g., pods or cuvettes) that are connected in sequence and separated by frangibles, with each receptacle containing a different reagent necessary for the intermediate reactions. The controller 140, 840, 999 of the respective dialysis machine 102, 802, 902 can control frangible breaking mechanisms corresponding to each of the frangibles separating the fluid receptacles in order to fluidly couple the receptacles in the proper sequence to perform the intermediate reactions required to generate the final reagent solution. The cuvettes 302, 304, 306, 702, 704, 852 or fluid receptacle 1002 are each attached to the chain of fluid receptacles and the final reagent solution is provided to the cuvettes 302, 304, 306, 702, 704, 852 or fluid receptacle 1002 for reacting with the spent dialysate, as described above.

While the emitters 342, 344, 346, 442, 444, 446, 742, 854, 1008 of the spent dialysate testing systems 300, 400, 500, 600, 700, 850, 1000 have been described as generating UV-vis radiation with wavelengths in a range of 400 nanometers to 700 nanometers, the emitters 342, 344, 346, 442, 444, 446, 742, 854, 1008 can be configured to produce other wavelengths of electromagnetic radiation for spectroscopic analysis of the solution contained within the respective cuvettes 302, 304, 306, 702, 704, 852 and fluid receptacle 1002. In some implementations, the emitters 342, 344, 346, 442, 444, 446, 742, 854, 1008 generate and transmit fluorescent light with wavelengths in a range of 100 nanometers to 1 millimeter through the solution contained within the respective cuvettes 302, 304, 306, 702, 704, 852 and fluid receptacle 1002 and the corresponding spectroscopy sensors 352, 354, 356, 452, 454, 456, 752, 856, 1010 detect the resulting electromagnetic spectrum. For example, in some implementations, the emitters 342, 344, 346, 442, 444, 446, 742, 854, 1008 generate and transmit ultraviolet light with wavelengths in a range of 100 nanometers to 400 nanometers through the solution contained within the respective cuvettes 302, 304, 306, 702, 704, 852 and fluid receptacle 1002, and the corresponding spectroscopy sensors 352, 354, 356, 452, 454, 456, 752, 856, 1010 detect the resulting electromagnetic spectrum. UV spectroscopic analysis of the electromagnetic radiation can then be applied to the electromagnetic spectrum detected by the spectroscopy sensors 352, 354, 356, 452, 454, 456, 752, 856, 1010 in order to determine a level of a particular waste product within the spent dialysate. In some implementations, the emitters 342, 344, 346, 442, 444, 446, 742, 854, 1008 generate and transmit infrared radiation with wavelengths in a range of 700 nanometers to 1 millimeter through the solution contained within the respective cuvettes 302, 304, 306, 702, 704, 852 and fluid receptacle 1002, and the corresponding spectroscopy sensors 352, 354, 356, 452, 454, 456, 752, 856, 1010 detect the resulting electromagnetic spectrum. Infrared spectroscopic analysis can then be applied to the electromagnetic spectrum detected by the spectroscopy sensors 352, 354, 356, 452, 454, 456, 752, 856, 1010 in order to determine a level of a particular waste product within the spent dialysate.

A number of embodiments have been described. Nevertheless, it will be understood that various modifications may be made without departing from the spirit and scope of the disclosure. Accordingly, other embodiments are within the scope of the following claims.

What is claimed is:

1. A method comprising:
   flowing spent dialysate through a spent dialysate line of a dialysis system into a fluid receptacle fluidly coupled to the spent dialysate line;
   reacting the spent dialysate with a chemical reagent contained within the fluid receptacle to generate a reacted sample;
   emitting electromagnetic radiation through the reacted sample using an emitter; and
   detecting a level of one or more waste products present in the spent dialysate using a spectroscopy sensor positioned proximate the fluid receptacle,
   wherein:
      flowing the spent dialysate from the spent dialysate line into the fluid receptacle comprises breaking a frangible connector to fluidly connect the spent dialysate line to the fluid receptacle; and
      the frangible connector is broken by a frangible breaking mechanism of a dialysis machine of the dialysis system.

2. The method of claim 1, wherein flowing the spent dialysate from the spent dialysate line into the fluid receptacle comprises:
   closing a first valve positioned along the spent dialysate line downstream of the fluid receptacle; and
   opening a second valve positioned along a fluid line fluidly coupling the spent dialysate line to the fluid receptacle.

3. The method of claim 2, further comprising:
   after a predetermined amount of time has elapsed since opening the second valve, closing the second valve and opening the first valve.

4. The method of claim 1, further comprising displaying, on a display device of a dialysis machine of the dialysis system, the level of the one or more waste products detected in the spent dialysate.

5. The method of claim 1, further comprising:
   determining that a threshold level of the one or more waste products is present in the spent dialysate; and
   in response, causing a dialysis machine of the dialysis system to generate an audible alert or a visual alert.

6. The method of claim 1, further comprising:
   determining that a threshold level of the one or more waste products is present in the spent dialysate; and
   in response, causing a dialysis machine of the dialysis system to transmit the detected level of the one or more waste products to a remote computing device.

7. The method of claim 1, further comprising mixing the spent dialysate and the chemical reagent by operating a stir bar within the fluid receptacle, applying vibrations to the fluid receptacle, or applying ultrasound pulses to the fluid receptacle.

8. The method of claim 1, wherein:
   the chemical reagent comprises a phosphate detection reagent; and detecting the level of one or more waste products present in the spent dialysate using the spectroscopy sensor comprises detecting a level of phosphate in the spent dialysate.

9. The method of claim 1, wherein:

the chemical reagent comprises an alizarin red solution; and detecting the level of one or more waste products present in the spent dialysate using the spectroscopy sensor comprises detecting a level of calcium in the spent dialysate.

10. The method of claim 1, wherein:

the chemical reagent comprises a picric acid solution; and detecting the level of one or more waste products present in the spent dialysate using the spectroscopy sensor comprises detecting a level of creatinine in the spent dialysate.

11. The method of claim 1, wherein:

the chemical reagent comprises a solution comprising crown ether 4-aminobenzo-18-crown-6 and crown ether modified gold nanoparticles; and detecting the level of one or more waste products present in the spent dialysate using the spectroscopy sensor comprises detecting a level of potassium in the spent dialysate.

12. The method of claim 1, wherein:

the chemical reagent comprises a Hg-EDTA solution; and detecting the level of one or more waste products present in the spent dialysate using the spectroscopy sensor comprises detecting a level of chloride present in the spent dialysate.

13. The method of claim 1, wherein the dialysis system comprises a hemodialysis machine and a dialyzer.

14. The method of claim 13, wherein flowing the spent dialysate from the spent dialysate line into the fluid receptacle comprises flowing the spent dialysate from the dialyzer, through the spent dialysate line, and into the fluid receptacle.

15. The method of claim 14, wherein a first portion of the spent dialysate flows into the fluid receptacle and a second portion of the spent dialysate flows to a drain coupled to the spent dialysate line.

16. The method of claim 1, wherein the dialysis system comprises a peritoneal dialysis machine and a dialysis fluid cassette configured to be coupled to the peritoneal dialysis machine.

17. The method of claim 16, wherein flowing the spent dialysate from the spent dialysate line of the dialysis machine into the fluid receptacle comprises flowing the spent dialysate from the dialysis fluid cassette, through the spent dialysate line of the peritoneal dialysis machine, and into the fluid receptacle.

18. The method of claim 16, wherein a first portion of the spent dialysate flows into the fluid receptacle and a second portion of the spent dialysate flows to a drain bag coupled to the spent dialysate line.

19. The method of claim 16, wherein:

at least a portion of the spent dialysate line is defined by the dialysis fluid cassette;

the fluid receptacle is defined by the dialysis fluid cassette; and flowing the spent dialysate from the spent dialysate line into the fluid receptacle comprises flowing spent dialysate within the dialysis fluid cassette into the fluid receptacle.

20. The method of claim 1, wherein:

the fluid receptacle is a first fluid receptacle;

the chemical reagent is a first chemical reagent;

the emitter is a first emitter;

the spectroscopy sensor is a first spectroscopy sensor; and the method further comprises:

flowing a second portion of the spent dialysate from the spent dialysate line of the dialysis system into a second fluid receptacle fluidly coupled to the spent dialysate line downstream of the first fluid receptacle;

reacting the spent dialysate with a second chemical reagent contained in the second fluid receptacle to generate a second reacted sample;

emitting electromagnetic radiation through the second reacted sample using a second emitter; and detecting a level of one or more waste products present in the second portion of the spent dialysate using a second spectroscopy sensor positioned proximate the second fluid receptacle.

21. The method of claim 1, wherein:

the fluid receptacle is a first fluid receptacle;

the chemical reagent is a first chemical reagent; and the method further comprises:

decoupling the first fluid receptacle from the spent dialysate line;

coupling a second fluid receptacle to the spent dialysate line of the dialysis system proximate the spectroscopy sensor and the emitter;

flowing a second portion of spent dialysate from the spent dialysate line into the second fluid receptacle;

reacting the spent dialysate with a second chemical reagent contained in the second fluid receptacle to generate a second reacted sample;

emitting electromagnetic radiation through the second reacted sample in the fluid receptacle using the emitter; and detecting a level of one or more waste products present in the spent dialysate using the spectroscopy sensor.

22. A dialysis system comprising a dialysis machine;

a spent dialysate line; and a spent dialysate testing system comprising:

a fluid receptacle configured to receive spent dialysate from the spent dialysate line;

a chemical reagent contained within the fluid receptacle and configured to react with the spent dialysate in the fluid receptacle to form a reacted sample;

an emitter positioned at a first end of the fluid receptacle and configured to emit electromagnetic radiation;

a spectroscopy sensor positioned at a second end of the fluid receptacle opposite the emitter and configured to detect an electromagnetic spectrum; and a frangible connector positioned between the fluid receptacle and the spent dialysate line, wherein:

the dialysis machine is configured to break the frangible connector in response to the dialysis machine receiving user input through a user interface of the dialysis machine;

breaking the frangible connector fluidly connects the spent dialysate line to the fluid receptacle and causes the spent dialysate to flow from the spent dialysate line into the fluid receptacle; and the frangible connector is broken by a frangible breaking mechanism of the dialysis machine of the dialysis system.

23. The dialysis system of claim 22, wherein the emitter comprises a light emitting diode.

24. The dialysis system of claim 22, wherein the emitter emits electromagnetic radiation in a range of 100 nanometers to 1 millimeter.

25. The dialysis system of claim 22, wherein the fluid receptacle comprises a transparent, rigid material.

26. The dialysis system of claim 22, wherein the fluid receptacle has a volume in a range of 1 milliliter to 3.5 milliliters.

27. The dialysis system of claim 22, wherein a distance between the emitter and the spectroscopy sensor is about 1 centimeter.

28. The dialysis system of claim 22, wherein the fluid receptacle comprises a vent.

\*    \*    \*    \*    \*